(12) United States Patent
Ding et al.

(10) Patent No.: US 6,458,783 B1
(45) Date of Patent: Oct. 1, 2002

(54) NON-IMIDAZOLE BENZODIAZEPINE INHIBITORS OF FARNESYL PROTEIN TRANSFERASE

(75) Inventors: Charles Z. Ding, Plainsboro; John T. Hunt, Princeton; Katerina Leftheris, Skillman, all of NJ (US); Rajeev S. Bhide, Langhorne, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/556,740

(22) Filed: Apr. 21, 2000

Related U.S. Application Data

(63) Continuation-in-part of application No. 09/161,801, filed on Sep. 28, 1998, now abandoned.
(60) Provisional application No. 60/060,823, filed on Sep. 29, 1997.

(51) Int. Cl.$^7$ .................... A61K 31/675; A61K 31/551; A61P 35/00; C07D 243/14
(52) U.S. Cl. .................... 514/220; 514/80; 514/221; 540/542; 540/557; 540/573
(58) Field of Search .................... 514/80, 220, 221; 540/542, 557, 573

(56) References Cited

U.S. PATENT DOCUMENTS

| | | | | | |
|---|---|---|---|---|---|
| 3,274,194 A | * | 9/1966 | Hayao | ..................... | 260/256.4 |
| 6,011,029 A | * | 1/2000 | Ding et al. | .................. | 514/221 |
| 6,071,903 A | * | 6/2000 | Albright et al. | ............ | 514/221 |

FOREIGN PATENT DOCUMENTS

| | | |
|---|---|---|
| WO | WO 94/26723 A | 11/1994 |
| WO | WO 95/32191 A | 11/1995 |
| WO | WO 97/30992 | 8/1997 |
| WO | WO 99/18951 A | 4/1999 |
| WO | WO 99/37625 A | 7/1999 |

OTHER PUBLICATIONS

Ayral–Kaloustian et al., Ras Farnesyltransferase Inhibitors, Annual Reports in Medicinal Chemistry, vol. 31, pp. 171–180, 1996.*

Balasubramanian et al., Recent Developments in Cancer Cytotoxics, Annual Reports in Medicinal Chemistry, vol. 33, pp. 151–159, 1998.*

Salmon et al., Principles of Cancer Therapy, Cecil Textbook of Medicine, W.B. Saunders Company, 20th Edition, pp. 1036–1049, 1996.*

* cited by examiner

*Primary Examiner*—Brenda Coleman
(74) *Attorney, Agent, or Firm*—Maureen S. Gibbons

(57) ABSTRACT

Inhibition of farnesyl transferase, which is an enzyme involved in ras oncogene expression, is effected by compounds of the formulas

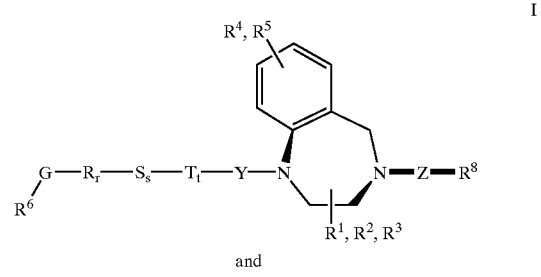

and

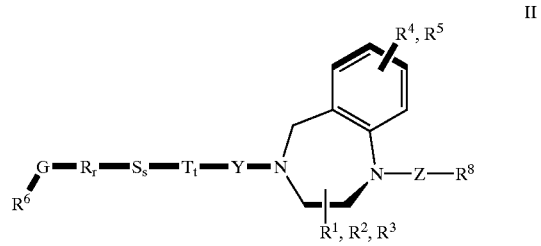

their enantiomers, diastereomers, and pharmaceutically acceptable salts, prodrugs and solvates thereof.

4 Claims, No Drawings

NON-IMIDAZOLE BENZODIAZEPINE INHIBITORS OF FARNESYL PROTEIN TRANSFERASE

RELATED APPLICATIONS

This application is a continuation-in-part of U.S. patent application Ser. No. 09/161,801, filed Sep. 28, 1998, now abandoned which claims priority benefit under Title 35 §119(e) of U.S. Provisional Patent Application Serial No. 60/060,823, filed Sep. 29, 1997.

FIELD OF THE INVENTION

This invention relates to compounds that inhibit farnesyl-protein transferase and ras protein farnesylation, thereby making them useful as anti-cancer agents. The compounds are also useful in the treatment of diseases, other than cancer, associated with signal transduction pathways operating through ras and those associated with proteins other than ras that are also post-translationally modified by the enzyme farnesyl protein transferase. The compounds may also act as inhibitors of other prenyl transferases, and thus be effective in the treatment of diseases associated with other prenyl modifications of proteins.

BACKGROUND OF THE INVENTION

The mammalian ras gene family comprises three genes, H-ras, K-ras and N-ras. The ras proteins are a family of GTP-binding and hydrolyzing proteins that regulate cell growth and differentiation. Overproduction of normal ras proteins or mutations that inhibit their GTPase activity can lead to uncontrolled cell division.

The transforming activity of ras is dependent on localization of the protein to plasma membranes. This membrane binding occurs via a series of post-translational modifications of the cytosolic Ras proteins. The first and mandatory step in this sequence of events is the farnesylation of these proteins. The reaction is catalyzed by the enzyme farnesyl protein transferase (FPT), and farnesyl pyrophosphate (FPP) serves as the farnesyl group donor in this reaction. The ras C-terminus contains a sequence motif termed a "Cys-Aaa$_1$-Aaa$_2$-Xaa" box (CAAX box), wherein Cys is cysteine, Aaa is an aliphatic amino acid, and Xaa is a serine or methionine. Farnesylation occurs on the cysteinyl residue of the CAAX box (cys-186), thereby attaching the prenyl group on the protein via a thio-ether linkage.

DESCRIPTION OF THE INVENTION

In accordance with the present invention, compounds of the formulas I, and

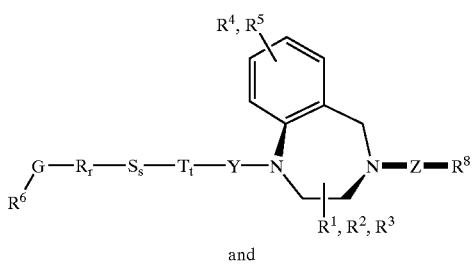

I and

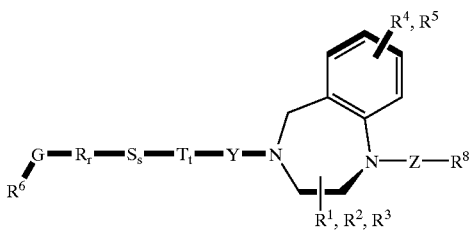

II

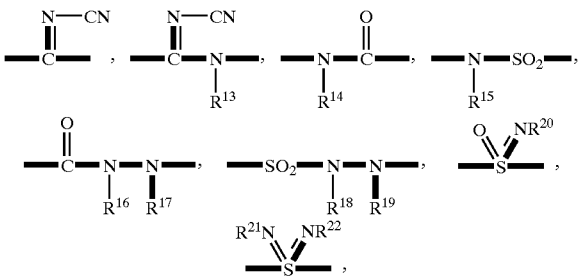

their enantiomers, diastereomers, and pharmaceutically acceptable salts, prodrugs and solvates thereof inhibit farnesyl protein transferase which is an enzyme involved in ras oncogene expression. In formulas I and II, and throughout the specification, the above symbols are defined as follows:

r, s and t are each independently 0 or 1;

Z is $CHR^9$, $SO_2$, CO, $CO_2$, O, $NR^{10}$, $—SO_2NR^{11}$, $—CONR^{12}$, or Z may be absent;

Y is $CHR^{23}$, $SO_2$, CO, $NR^{24}$, $—SO_2NR^{25}$ or $—CONR^{26}$ or Y may be absent;

$R^6$, $R^9$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{41}$, $R^{42}$, $R^{43}$, $R^{44}$, $R^{45}$ and $R^{46}$ are each independently hydrogen, lower alkyl, substituted alkyl, aryl or substituted aryl;

$R^4$, $R^5$, $R^{47}$, $R^{48}$, $R^{49}$, $R^{50}$ and $R^{51}$ are each independently hydrogen, halo, nitro, cyano or $U-R^{27}$;

U is sulfur, oxygen, $NR^{28}$, CO, SO, $SO_2$, $CO_2$, $NR^{29}CO_2$, $NR^{30}CONR^{31}$, $NR^{32}SO_2$, $NR^{33}SO_2NR^{34}$, $SO_2NR^{35}$, $NR^{36}CO$, $CONR^{37}$, $PO_2R^{38}$ or $PO_3R^{39}$ or U is absent;

$R^4$ and $R^5$ may join together to form a ring;

$R^1$, $R^2$ and $R^3$ are each independently hydrogen, alkyl, alkoxycarbonyl, substituted alkyl, alkenyl, substituted alkenyl, alkynyl, substituted alkynyl, aralkyl, cycloalkyl, aryl, substituted aryl, heterocyclo, substituted heterocyclo, cyano, carboxy, carbamyl or substituted carbamyl;

$R^8$ and $R^{27}$ are each independently hydrogen, alkyl, substituted alkyl, alkenyl, substituted alkenyl, alkynyl, substituted alkynyl, aralkyl, cycloalkyl, aryl, substituted aryl, heterocyclo or substituted heterocyclo;

any two of $R^1$, $R^2$ and $R^3$ may join to form a cycloalkyl group;

R, S and T are each independently $CR^{40}R^{41}$ or $NR^{42}$;

$R^{40}$ is H, $NR^{44}R^{45}$, $OR^{46}$ or CN;

G is $—S—$, $—SO_2NH—$, $—NHSO_2—$, $—N(OR^{46})SO_2—$,

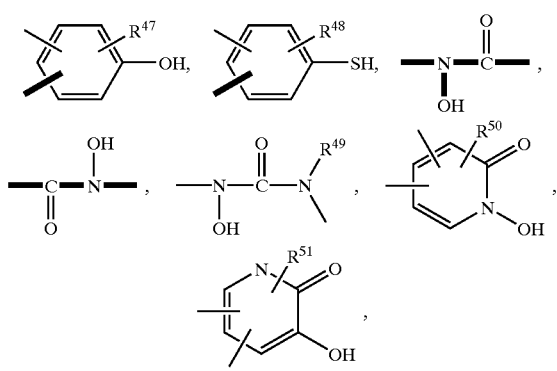

or heterocycles other than imidazole;
with the provisos that:
1) $R^{27}$ may be hydrogen except when U is SO, $SO_2$, $CO_2$, $NR^{29}CO_2$ or $NR^{32}SO_2$, or
2) $R^8$ may be hydrogen except when Z is $SO_2$, $CO_2$,

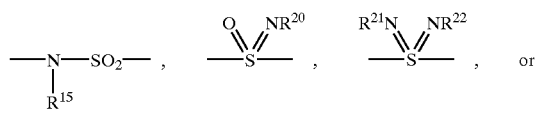

3) only one of Y, R, S and T may be nitrogen, or
4) any of Y, R, S and T may be nitrogen except when G is —S—, —$NHSO_2$—, —$N(OR^{46})SO_2$—,

or
5) $R^6$ may be hydrogen except when G is —$NHSO_2$— or —$N(OR^{46})SO_2$—, or
6) the sum of r, s and t together may not be zero.

Listed below are definitions of various terms used to describe this invention. These definitions apply to the terms as they are used throughout this specification, unless otherwise limited in specific instances, either individually or as part of a larger group.

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms.

The term "substituted alkyl" refers to an alkyl group substituted by, for example, one to four substituents, such as, halo, trifluoromethyl, trifluoromethoxy, hydroxy, alkoxy, cycloalkoxy, heterocyclooxy, oxo, alkanoyl, aryloxy, alkanoyloxy, amino, alkylamino, arylamino, aralkylamino, cycloalkylamino, heterocycloamino, disubstituted amines in which the 2 amino substituents are selected from alkyl, aryl or aralkyl; alkanoylamino, aroylamino, aralkanoylamino, substituted alkanoylamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido, e.g. $SO_2NH_2$, substituted sulfonamido, nitro, cyano, carboxy, carbamyl, e.g. $CONH_2$, substituted carbamyl e.g. CONH alkyl, CONH aryl, CONH aralkyl or cases where there are two substituents on the nitrogen selected from alkyl, aryl or aralkyl; alkoxycarbonyl, aryl, substituted aryl, guanidino and heterocyclos, such as, indolyl, imidazolyl, furyl, thienyl, thiazolyl, pyrrolidyl, pyridyl, pyrimidyl and the like. Where noted above where the substituent is further substituted it will be with halogen, alkyl, alkoxy, aryl or aralkyl.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "aralkyl" refers to an aryl group bonded directly through an alkyl group, such as benzyl.

The term "substituted aryl" refers to an aryl group substituted by, for example, one to four substituents such as alkyl, substituted alkyl, halo, trifluoromethoxy, trifluoromethyl, hydroxy, alkoxy, cycloalkyloxy, heterocyclooxy, alkanoyl, alkanoyloxy, amino, alkylamino, aralkylamino, cycloalkylamino, heterocycloamino, dialkylamino, alkanoylamino, thiol, alkylthio, cycloalkylthio, heterocyclothio, ureido, nitro, cyano, carboxy, carboxyalkyl, carbamyl, alkoxycarbonyl, alkylthiono, arylthiono, alkysulfonyl, sulfonamido, aryloxy and the like. The substituent may be further substituted by halo, hydroxy, alkyl, alkoxy, aryl, substituted aryl, substituted alkyl or aralkyl.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "substituted alkenyl" refers to an alkenyl group substituted by, for example, one to two substituents, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclo, e.g. indolyl, imidazolyl, furyl, thienyl, thiazolyl, pyrrolidyl, pyridyl, pyrimidyl and the like.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "substituted alkynyl" refers to an alkynyl group substituted by, for example, a substituent, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclo, e.g. imidazolyl, furyl, thienyl, thiazolyl, pyrrolidyl, pyridyl, pyrimidyl and the like.

The term "cycloalkyl" refers to a optionally substituted, saturated cyclic hydrocarbon ring systems, preferably containing 1 to 3 rings and 3 to 7 carbons per ring which may be further fused with an unsaturated $C_3$–$C_7$ carbocyclic ring. Exemplary groups include cyclopropyl, cyclobutyl, cyclopentyl, cyclohexyl, cycloheptyl, cycloctyl, cyclodecyl, cyclododecyl, and adamantyl. Exemplary substituents include one or more alkyl groups as described above, or one or more groups described above as alkyl substituents.

The terms "heterocycle", "heterocyclic" and "heterocyclo" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2, 3, or 4 heteroatoms selected from nitrogen, oxygen and sulfur, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydrothiopyranyl, tetrahydropyranyl, morpholinyl, thiamorpholinyl, thiamorpholinyl sulfoxide, tetrahydrothiopyranylsulfone, thiamorpholinyl sulfone, 1,3-dioxolane and tetrahydro-1,1-dioxothienyl, dioxanyl, isothiazolidinyl, thietanyl, thiiranyl, triazinyl, and triazolyl, and the like. Also included are smaller heterocyclos, such as, epoxides and aziridines.

Exemplary bicyclic heterocyclic groups include benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b] pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents include one or more alkyl groups as described above or one or more groups described above as alkyl substituents.

The term "heteroatoms" shall include oxygen, sulfur and nitrogen.

The compounds of formulas I–II may form salts which are also within the scope of this invention. Pharmaceutically acceptable (i.e. non-toxic, physiologically acceptable) salts are preferred, although other salts are also useful, e.g., in isolating or purifying the compounds of this invention.

The compounds of formulas I–II may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts may be obtained, for example, by exchanging the carboxylic acid protons, if they contain a carboxylic acid, in compounds I–II with the desired ion in a medium in which the salt precipitates or in an aqueous medium followed by evaporation. Other salts can be formed as known to those skilled in the art.

The compounds for formulas I–II may form salts with a variety of organic and inorganic acids. Such salts include those formed with hydrogen chloride, hydroxy methane sulfonic acid, hydrogen bromide, methanesulfonic acid, sulfuric acid, acetic acid, trifluoroacetic acid, maleic acid, benzenesulfonic acid, toluenesulfonic acid and various others (e.g., nitrates, phosphates, borates, tartrates, citrates, succinates, benzoates, ascorbates, salicylates and the like). Such salts may be formed by reacting compounds I–II in an equivalent amount of the acid in a medium in which the salt precipitates or in an aqueous medium followed by evaporation.

In addition, zwitterions ("inner salts") may be formed.

Compounds of the formulas I–II may also have prodrug forms. Any compound that will be converted in vivo to provide the bioactive agent (i.e., the compound for formulas I–II) is a prodrug within the scope and spirit of the invention.

For example compounds of the formulas I–II may be a carboxylate ester moiety. The carboxylate ester may be conveniently formed by esterifying any of the carboxylic acid functionalities found on the disclosed ring structure(s).

Various forms of prodrugs are well known in the art. For examples of such prodrug derivatives, see:

a) *Design of Prodrugs*, edited by H. Bundgaard, (Elsevier, 1985) and *Methods in Enzymology*, Vol.42, p. 309–396, edited by K. Widder, et al. (Acamedic Press, 1985);

b) *A Textbook of Drug Design and Development*, edited by Krosgaard-Larsen and H. Bundgaard, Chapter 5, "Design and Application of Prodrugs," by H. Bundgaard, p. 113–191 (1991);

c) H. Bundgaard, *Advanced Drug Delivery Reviews*, 8, 1–38 (1992);

d) H. Bundgaard, et al., *Journal of Pharmaceutical Sciences*, 77, 285 (1988); and e) N. Kakeya, et al., *Chem Phar Bull*, 32, 692 (1984).

It should further be understood that solvates (e.g., hydrates) of the compounds of formulas I–IV are also with the scope of the present invention. Methods of solvation are generally known in the art.

Use and Utility

The compounds of formulas I–II are inhibitors of S-farnesyl protein transferase. They are thus useful in the treatment of a variety of cancers, including (but not limited to) the following;

carcinoma, including that of the bladder, breast, colon, kidney, liver, lung, including small cell lung cancer, ovary, prostate, testes, pancreas, esophagus, stomach, gall bladder, cervix, thyroid and skin, including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, and Burketts lymphoma;

hematopoietic tumors of myeloid lineage, including acute and chronic myelogenous leukemias, myelodysplastic syndrome and promyelocytic leukemia;

tumors of the central and peripheral nervous system, including astrocytoma, neuroblastoma, glioma, and schwannomas;

tumors of mesenchymal origin, including fibrosarcoma, rhabdomyoscarcoma, and osteosarcoma;

other tumors, including melanoma, xenoderma pigmentosum, keratoactanthoma, seminoma, thyroid follicular cancer and teratocarcinoma.

The compounds of formulas I–II are especially useful in treatment of tumors having a high incidence of ras involvement, such as colon, lung, and pancreatic tumors and in tumors in which a prenyl transferase contributes to tumor maintenance, tumor growth or tumor development. By the administration of a composition having one (or a combination) of the compounds of this invention, development of tumors in a mammalian host is reduced, or tumor burden is reduced, or tumor regression is produced.

Compounds of formulas I–II may also inhibit tumor angiogenesis, thereby affecting the growth of tumors. Such anti-angiogenesis properties of the compounds of formulas I–II may also be useful in the treatment of certain forms of blindness related to retinal vascularization.

Compounds of formulas I–II may also be useful in the treatment of diseases other than cancer that may be associated with signal transduction pathways operating through ras, e.g., neurofibromatosis, atherosclerosis, pulmonary fibrosis, arthritis, psoriasis, glomerulonephritis, restenosis following angioplasty or vascular surgery, hypertrophic scar formation, polycystic kidney disease and endotoxic shock. Compounds I–II may be useful as anti-fungal agents.

Compounds of formula I–II may induce or inhibit apoptosis, a physiological cell death process critical for normal development and homeostasis. Alterations of apoptotic pathways contribute to the pathogenesis of a variety of human diseases. Compounds of formula I–II, as modulators of apoptosis, will be useful in the treatment of a variety of human diseases with aberrations in apoptosis including cancer (particularly, but not limited to follicular lymphomas, carcinomas with p53 mutations, hormone dependent tumors of the breast, prostrate and ovary, and precancerous lesions such as familial adenomatous polyposis), viral infections (including but not limited to herpes virus, pox virus, Epstein-Barr virus, Sindbis virus and adenovirus), autoimmune diseases (including but not limited to systemic lupus erythematosus, immune mediated glomerulonephritis, rheumatoid arthritis, psoriasis, inflammatory bowel diseases and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), AIDS, myelodysplastic syndromes, aplastic anemia, ischemic injury associated myocardial infarctions, stroke and reperfusion injury, arrhythmia, atherosclerosis, toxin-induced or alcohol induced liver diseases, hematological diseases (including but not limited to chronic anemia and aplastic anemia), degenerative diseases of the musculoskeletal system (including but not limited to osteoporosis and arthritis), aspirin-sensitive rhinosinusitis, cystic fibrosis, multiple sclerosis, kidney diseases, and cancer pain.

Compounds of formulas I–II may also be useful in the treatment of diseases associated with farnesyl transferase substrates other than ras (e.g., nuclear lamins, transducin, rhodopsin kinase, cGMP phosphodiesterase, TC21, phosphorylase kinase, Rap2, RhoB, RhoE, PRL1) that are also post-translationally modified by the enzyme farnesyl protein transferase.

Compounds of formulas I–II may also act as inhibitors of other prenyl transferases (e.g., geranylgeranyl transferase I and II), and thus be effective in the treatment of diseases associated with other prenyl modifications (e.g., geranylgeranylation) of proteins (e.g. the rap, rab, rac and rho gene products and the like). For example, they may find use as drugs against Hepatitis delta virus (HDV) infections, as suggested by the recent finding that geranylgeranylation of the large isoform of the delta antigen of HDV is a requirement for productive viral infection [J. S. Glen, et al., Science, 256, 1331 (1992)].

The compounds of this invention may also be useful in combination with known anti-cancer and cytotoxic agents and treatments, including radiation. If formulated as a fixed dose, such combination products employ the compounds of this invention within the dosage range described below and the other pharmaceutically active agent within its approved dosage range. Compounds of formulas I–II may be used sequentially with known anticancer or cytotoxic agents and treatment, including radiation when a combination formulation is inappropriate.

Farnesyl transferase assays were performed as described in V. Manne et al., Drug Development Research, 34, 121–137, (1995). The compounds of Examples 1–17 inhibited farnesyl transferase with IC 50 values between 0.1 nM and 100 uM.

The compounds of this invention may be formulated with a pharmaceutical vehicle or diluent for oral, intravenous, intraperitoneal, subcutaneous, intraabdominal, intramuscular, rectal, vaginal or topical administration. Oral administration may involve the use of slow release formulations, such as biodegradable polymers or prodrugs. The pharmaceutical composition can be formulated in a classical manner using solid or liquid vehicles, diluents and additives appropriate to the desired mode of administration. Orally, the compounds can be administered in the form of tablets, capsules, granules, powders and the like. The compounds may be administered in a dosage range of about 0.05 to 200 mg/kg/day, preferably less than 100 mg/kg/day, in a single dose or in 2 to 4 divided doses.

Process of Preparation

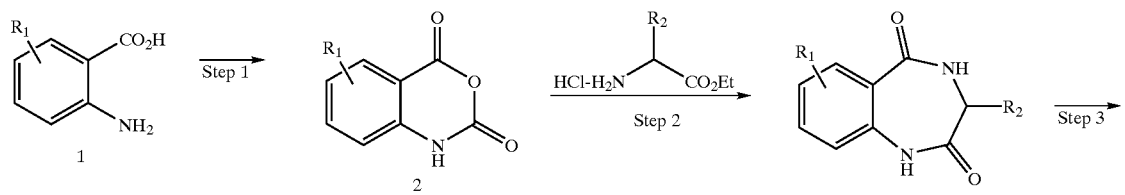

Scheme 1

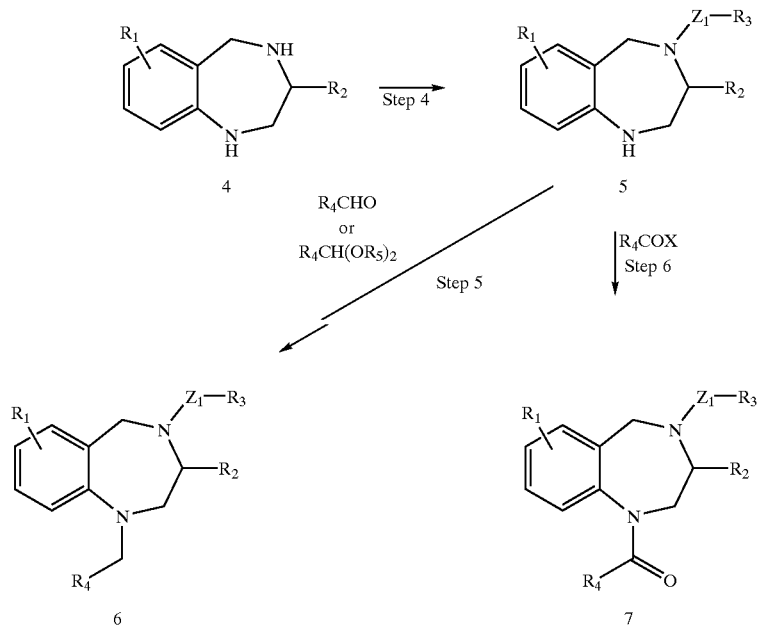

wherein $R_1$ is selected from H, halo, $NO_2$, $NH_2$, CN, alkyl, aryl, heteroaryl, substituted alkyl, arylalkyl, alkoxy and substituted amino; $R_2$, $R_3$ and $R_4$ are selected from alkyl, substituted alkyl, arylalkyl, aryl, heteroaryl; $R_2$ can also be hydrogen; $Z_1$ is selected from CO, $SO_2$, $CO_2$, $CONR^5$, $SO_2NR^5$.

Step 1

The isatoic anhydride 2 was formed by reaction of optionally substituted anthranilic acid with a phosgene equivalent, such as, phosgene or triphosgene in a mixed aqueous/organic solvent at from 0° C. to 50° C. range.

Step 2

The isatoic anhydride 2 is reacted with an amino acid ester hydrochloride salt in pyridine at an elevated temperature with reflux as preferred to give benzodiazepinedione 3. The compound 3 wherein $R_1$ is aryl or heteroaryl can be prepared from the compound 3 wherein $R_1$ is bromo by a palladium coupling of an aryl or heteroaryl metaloid derivative such as phenylboronic acid in a mixed aqueous/organic solvent, e.g. THF/DMF/water, in the presence of a base, e.g. sodium carbonate, at from room temperature to 110° C. The compound 3 wherein $R_1$ is a nitrile can be prepared from the compound 3 wherein $R_1$ is bromo by reaction with copper cyanide in an organic solvent such as N-methylpyrrolidinone at room temperature to 250° C.

Step 3

Thereafter the compound 3 is reacted with a reducing agent such as lithium aluminum hydride or borane in an inert atmosphere and in an organic solvent, such as, tetrahydrofuran at from room temperature to reflux.

Step 4

Thereafter the product is acylated or sulfonylated under standard conditions at from −78° C. to 100° C. (e.g., by reaction with an acid halide $R_3COX$ wherein X is Cl or Br in an inert organic solvent, e.g. acetonitrile, or in a mixed aqueous/organic solvent e.g. NaOH/dichloroethane; by reaction with a sulfonyl halide $R_3SO_2X$ or sulfamyl halide $R_3(R_5)NSO_2X$ wherein X is Cl or Br in an organic solvent such as THF in the presence of a base such as diisopropylethylamine or in a mixed aqueous/organic solvent e.g. $NaOH/CH_2Cl_2$). Where the compound 5 is sulfonylated with a beta-haloalkylsulfonyl halide, the halide may then be eliminated by a base such as diisopropylethylamine and then nucleophiles such as dimethylamine may be added to the resulting unsaturated sulfonamide by treatment in an organic solvent such as THF or dichloromethane at from room temperature to reflux.

Step 5

(a) Thereafter the various products can undergo reductive alkylation with an aldehyde in the presence of an acid e.g. acetic acid, a reducing agent e.g. $NaBH(OAc)_3$ in an inert organic solvent e.g. dichloroethane at about room temperature to form the compounds of formula I and II. The aldehydes may be prepared from the appropriate alcohols by oxidation with for example oxalyl chloride/DMSO/triethylamine. They may be prepared from appropriate carboxylic acid derivatives such as esters by reduction with for example diisobutylaluminum hydride in an organic solvent such as methylene chloride at from −78° C. to room temperature.

(b) Compound 6 may be further manipulated to give the compounds of formula I and II, such as by reaction with a deprotecting agent like TFA/triethylsilane in an organic solvent such as dichloroethane.

(c) If the compound 6 contains a leaving group such as chloride or bromide; or, in the case of a hydroxyl group, such a group may be transformed into a leaving group such as trifluoromethanesulfonate; the compound may be reacted with a nucleaphile such as 2-aminopyridine to give the desired compounds of formula I or II. Alternatively, the compound 6 may be reacted with thiourea, triphenylmethane mercaptan or sodium azide to afford an intermediate which may be subsequently transformed using standard conditions to desired compounds of formula I or II.

Step 6

The compound 5 is acylated with an acylating agent such as an acid chloride in a solvent such as methylene chloride in the presence of an optional base such as diisopropylethylamine. The compound 5 may also be acylated with an isocyanate which in turn can be prepared by an acyl azide like nicotinoyl azide. If $R_4$ contains a leaving group such as chloride, the compound may be further reacted with nucleophile such as 2-pyrrolidinone or ammonia to form the compounds of formula I or II.

The invention will now be further described by the following working examples, which are preferred embodiments of the invention. All temperatures are in degrees Celsius (° C.) unless otherwise indicated. These examples are illustrative rather than limiting.

Scheme 2

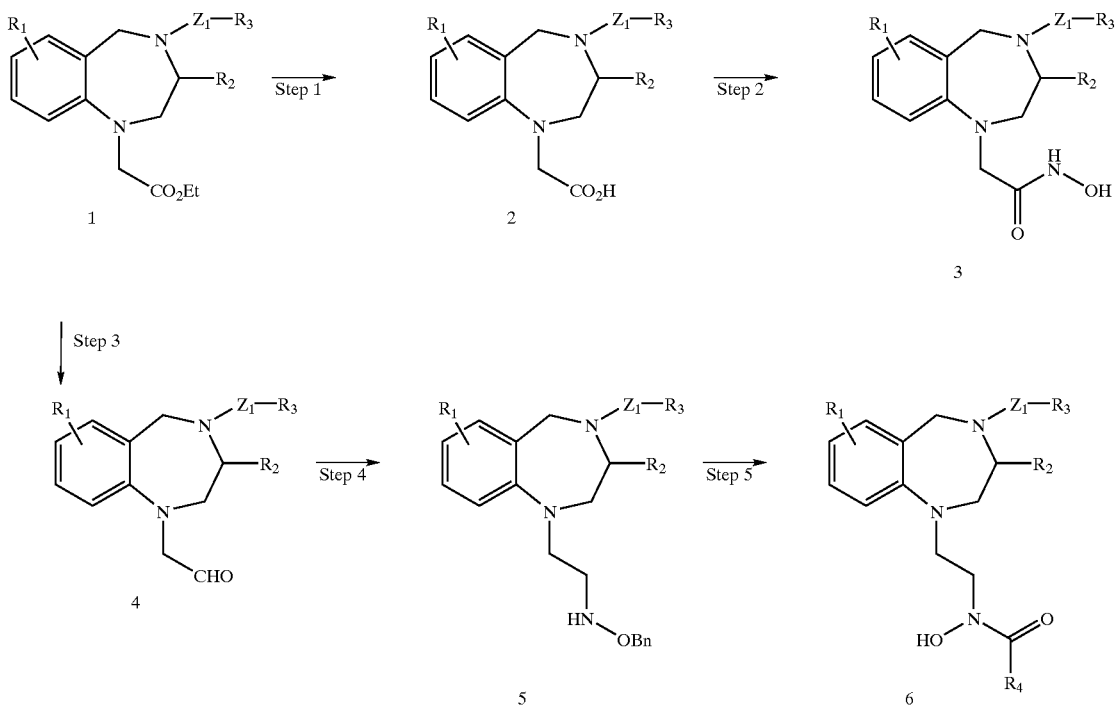

wherein $R_1$ is selected from H, halo, $NO_2$, $NH_2$, CN, alkyl, aryl, heteroaryl, substituted alkyl, arylalkyl, alkoxy and substituted amino; $R_2$, $R_3$ and $R_4$ are selected from alkyl, arylalkyl, aryl, heteroaryl; $R_2$ and $R_4$ can also be hydrogen; $R_4$ can also be amino; Z is selected from CO, $SO_2$, $CO_2$, $CONR^5$, $SO_2NR^5$.

Step 1

An ester 1 prepared by following Step 5 of Scheme 1 may be saponified to an acid 2 with a base such as LiOH in a solvent such as aq. methanol in THF at about room temperature.

Step 2

Thereafter the acid 2 is converted to hydroxamic acid 3 with hydroxylamine hydrochloride in the presence of a dehydrating agent such as 1-(3-dimethylaminopropyl)-3-ethylcarbodiimide hydrochloride and a base such as triethylamine.

Step 3

The ester 1 may be reduced to an aldehyde 4 by a reducing agent such as diisobutylaluminium hydride in an organic solvent such as methylene chloride.

Step 4

Thereafter, the aldehyde 4 may be reductively aminated with a hydroxylamine derivative such as O-benzyl hydroxylamine and a reducing agent such as sodium cyanoborohydride to give 5.

Step 5

The compound 5 may be acylated with an acylating agent such as formic anhydride to give after deprotection, e.g., by hydrogenation the compound 6.

EXAMPLE 1

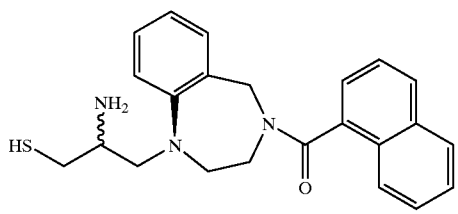

(+,−)-1-(2-Amino-3-mercaptopropyl)-2,3,4,5-tetrahydro-4-(naphthalenylcarbonyl)-1H-1,4-benzodiazepine, Monohydrochloride A. 2,3,4,5-Tetrahydro-1H-benzodiazepine-2,5-dione.

A stirred solution of isatoic anhydride (16.4 g, 0.1 mol) and glycine ethyl ester hydrochloride in 40 mL of pyridine was heated under reflux on an oil-bath for 7 h. The suspension was cooled to 0° C. for 18 h. The precipitate was collected, and washed with ethanol and ether to give a light yellow solid (7.0 g, 40%).

B. 2,3,4,5H-Tetrahydro-1-1,4-benzodiazepine

To a stirred suspension of LAH (3.5 g, 90 mmol) in THF (100 mL) at room temperature was slowly added compound A (3.5 g, 20 mmol) portionwise at room temperature under argon. The resultant suspension was heated on an oil-bath at reflux under argon for 18 h and cooled to 0° C. A solution of ammonium hydroxide (5 mL, conc.) in 30 mL of THF was added via an additional funnel. The resultant suspension was stirred for 1 h and filtered. The filtrate was concentrated in vacuo to give an oil (2.5 g, 84%).

C. 2,3,4,5-Tetrahydro-4-(naphthalenylcarbonyl)-1H-1,4-benzodiazepine

To a stirred solution of the compound B (2.0 g, 13.4 mmol) in a mixed solvent of $CH_2Cl_2$/1N NaOH (1:1, 150 mL), a solution of 1-naphthoyl chloride (2.0 ml, 13.4 mmol) in $CH_2Cl_2$ (3 mL) was added slowly at 0° C. The biphasic mixture was allowed to stir at 0° C. for 2 hr. The aqueous phase was extracted with $CH_2Cl_2$ (2×100 mL). The combined organic layers were dried over $Na_2SO_4$, concentrated to provide the title compound (3.6 g, 89%) as a white solid. MS (M+H) 303. Anal. cal'd for $C_{20}H_{18}N_2O$: C, 89.44; H, 6.00; N, 9.26. Found: C, 89.48; H, 5.98; N, 9.14.

D. (+,−)-1-(2-Amino-3-mercaptopropyl)-2,3,4,5-tetrahydro-4-(naphthalenylcarbonyl)-1H-1,4-benzodiazepine, Monohydrochloride To a stirred solution of compound C (102 mg, 0.34 mmol) and N-BOC-S-trityl-cysteine aldehyde (170 mg, 0.38 mmol) in a mixture of dichloroethane (5 mL) and acetic acid (0.5 mL), was added $NaBH(OAc)_3$ (150 mg, 0.68 mmol) in one portion. The reaction was allowed to proceed for 30 min, the mixture was diluted with ethyl acetate (50 mL), followed by addition of sat. $NaHCO_3$ (5 mL). The resultant mixture was stirred for 2 h, and poured into a mixture of ethyl acetate and saturated $NaHCO_3$ and well shaken. The organic layer was separated, and the aqueous layer was extracted with ethyl acetate (50 mL). The combined organic extracts were dried over $MgSO_4$ and concentrated in vacuo. The residue was purified by flash column chromatography (1:2 ethyl acetate and hexanes) to give an oil (220 mg, 88%). This was dissolved in a solvent of TFA and methylene chloride (5 mL, 1:1). The resultant solution was stirred at room temperature for 3 h. The solvent was removed in vacuo and the residue was partitioned in ether (10 mL) and 10% HCl solution (10 mL). The aqueous solution was separated, and concentrated in vacuo to a small volume. The product was purified by preparative HPLC (aqueous methanol in the presence of 0.1%TFA) and obtained as HCl salt after salt exchange (73 mg, 62%, mp: 140° C.). MS (M+H) 392.

EXAMPLE 2

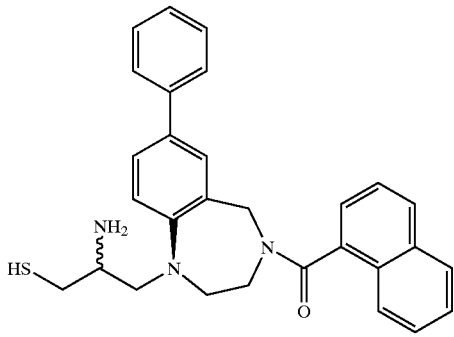

(+,−)-1-(2-Amino-3-mercaptopropyl)-2,3,4,5-tetrahydro-4-(naphthalenylcarbonyl)-7-phenyl-1H-1,4-benzodiazepine, Monohydrochloride A. 5-Bromoisatoic Anhydride To a stirred solution of 5-bromo-2-amino-benzoic acid (25 g, 0.115 mmol) in a mixed solvent of THF:$H_2O$:conc. HCl (4:2:1, 350 mL), was added a solution of phosgene (0.23 mmol, 20% in toluene) dropwise. The reaction mixture was allowed to stir at room temperature for 4 h. The resulting precipitate was filtered, washed with water and dried under reduced pressure to give the title compound (22.5 g, 78%) as a gray solid.

B. 2,3,4,5-Tetrahydro-7-bromo-1H-1,4-benzodiazepine-2,5-dione

The title compound was prepared by following the procedure for the preparation of compound A of Example 1.

C. 2,3,4,5-Tetrahydro-7-phenyl-1H-1,4-benzodiazepine-2,5-dione

To a stirred, degassed solution of compound B (13.0 g, 51 mmol) in a solvent of DMF/THF (1:2, 250 mL), tetrakis (triphenyl phosphine) palladium(0) (10.5 g, 9.1 mmol) was added. After stirring for 0.5 hr, an aqueous solution of $Na_2CO_3$ (8.5 g, 80 mmol) was added followed by benzeneboronic acid (10.2 g, 83 mmol). The resultant suspension was heated at 105° C. for 24 hrs and filtered. The filtrate was concentrated and diluted with $H_2O$ (200 mL). The precipitate was filtered, and washed with $H_2O$ (200 mL), $CH_2Cl_2$ (50 mL) and ethyl acetate (100 mL) to afford the title compound as a yellow solid (10.8 g, 81%). MS (M+H) 253.

D. 2,3,4,5-Tetrahydro-7-phenyl-1H-1,4-benzodiazepine

The title compound was prepared by following the procedure for the preparation of compound B of Example 1. MS (M+H) 225.

E. 2,3,4,5-Tetrahydro-4-(naphthalenylcarbonyl)-7-phenyl-1H-1,4-benzodiazepine

The title compound was prepared by following the procedure for the reparation of compound C of Example 1. MS (M−H) 379.

F. (+,−)-1-(2-Amino-3-mercaptopropyl)-2,3,4,5-tetrahydro-4-naphthalenylcarbonyl)-7-phenyl-1H-1,4-benzodiazepine, Monohydrochloride The title compound was prepared by following the procedure for the preparation of compound D of Example 1. MS (M+H): 468.

EXAMPLE 3

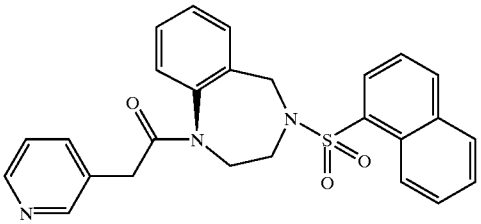

2,3,4,5-Tetrahydro-4-(1-naphthalenylsulfonyl)-N-(3-pyridinyl)-1-1,4-benzodiazepine-1-carboxamide A. 2,3,4,5-Tetrahydro-4-(1-naphthalenylsulfonyl)-1-1,4-benzodiazepine To a stirred solution of the compound B of Example 1 (0.75 g, 5.0 mmol) in methylene chloride and 1 N NaOH solution (30 mL, 3:1) at 0° C., was added 1-naphthalenesulfonyl chloride (1.13 g, 5.0 mmol). The mixture was allowed to stir at 0° C. for 30 min and poured into a mixture of methylene chloride and 1 NaOH solution (50 mL each). The organic layer was separated and washed with $NH_4Cl$ solution, dried over $MgSO_4$ and concentrated in vacuo. The residue was crystallized from methanol to give a solid (1.3 g, 78%, mp: 165–166° C.). MS (M+H): 339.

B. 2,3,4,5-Tetrahydro-4-(1-naphthalenylsulfonyl)-N-(3-pyridinyl)-1H-1,4-benzodiazepine-1-carboxamide A stirred solution of the compound A (160 mg, 0.47 mmol), and 3-nicotinyl azide (90 mg, 0.61 mmol) in toluene (2 mL) was heated at 100° C. for 3 h. The mixture was cooled to room temperature. The solvent was removed in vacuo and the residue was crystallized from ether to give a white solid (150 mg, 70%). MS (M+H): 459.

Anal. calc'd $C_{25}H_{22}N_4O_3S \cdot 0.30H_2O$: C, 64.72; H, 4.91; N, 12.08; S, 6.91. Found: C, 64.63; H, 4.89; N, 11.86; S, 6.54.

EXAMPLE 4

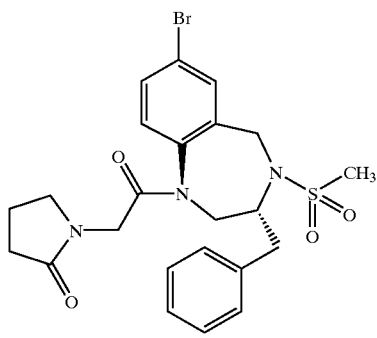

(R)-7-Bromo-2,3,4,5-tetrahydro-4-(methylsulfonyl)-1-[(2-oxo-1-pyrrolidinyl)acetyl]-3-(phenylmethyl)-1H-1,4-benzodiazepine, Trifluoroacetate A. (R)-2,3,4,5-Tetrahydro-7-bromo-3-phenylmethyl-benzodiazapine-2,5-dione A stirred solution of the compound A of Example 2 (150 g, 0.62 mol) and D-phenyl alanine methyl ester hydrochloride (127.3 g, 0.59 mol) in the presence of 4-dimethylaminopyridine (2 g) in pyridine (1500 mL) was heated at reflux under argon for 3 days. The pyridine was removed in vacuo and the residue was dissolved in methylene chloride (3 L). The solution was washed with 10% HCl solution and brine, dried, and concentrated in vacuo to a small volume. The solid thus formed was collected and dried to give 152 g of solid (mp: 242–243° C.; 71%).

B. (R)-2,3,4,5-Tetrahydro-7-bromo-3-phenylmethyl-benzodiazapine

To a stirred solution of compound A (30 g, 87 mmol) in anhydrous THF (870 mL) under argon, was added a solution of borane tetrahydrofuran complex (440 mL of a 1 M solution, 440 mmol) at room temperature. The solution was slowly heated to reflux, and maintained at reflux for 18 h. The mixture was cooled to 0° C., and methanol (150 mL) was added slowly. The resultant solution was concentrated in vacuo. The residue was dissolved in methanol (250 mL) and 7 N HCl solution (50 mL) was added. The mixture was heated on a steam-bath for 2 h. The solid thus formed was collected, resuspended in water (400 mL) and the aqueous suspension was made basic to pH 11 with 5 N NaOH solution and extracted with ethyl acetate (2×300 mL). The organic extracts were combined, dried, concentrated in vacuo and the residue was crystallized from methanol and water (9:1) to give a white solid (mp: 135–138° C., 25 g, 91%).

C. (R)-2,3,4,5-Tetrahydro-7-bromo-4-methanesulfonyl-3-phenylmethyl-benzodiazapine To a stirred solution of compound B (1.5 g, 4.73 mmol), pyridine (3 mL), and diisopropylethyl amine (1.6 mL, 9.46 mmol) in methylene chloride, was added methanesulfonyl chloride (0.55 mL, 7.11 mmol) at 0° C. under argon. The resultant mixture was allowed to stir at 0° C. for 2 h, 1 N NaOH solution (30 mL) was added and the mixture was stirred for 2 h. The organic layer was separated, washed with 1 N HCl solution (2×100 mL), dried, and concentrated in vacuo to give a yellow solid (1.7 g, 91%).

D. (R)-7-Bromo-2,3,4,5-tetrahydro-4-(methylsulfonyl)-1-chloroacetyl-3-(phenylmethyl)-1-1,4-benzodiazepine To a stirred solution of compound C (2.0 g, 5.06 mmol) and diisopropylethylamine (4.4 mL, 25 mmol) in dichloromethane (100 mL) in an ice bath under argon, was added chloroacetyl chloride (2.0 mL, 25.3 mmol). The mixture was allowed to stir for 30 min., poured into 1N aqueous sodium hydroxide solution (200 mL) and extracted with dichloromethane (2×100 mL). The organic extracts were combined, washed with 10% HCl solution and brine, dried (MgSO$_4$) and concentrated in vacuo to an oil, which was purified by chromatography (3:1, hexane:ethylacetate) to give the title compound as a colorless oil (760 mg, 33%).

E. (R)-7-Bromo-2,3,4,5-tetrahydro-4-(methylsulfonyl)-1-[(2-oxo-1-pyrrolidinyl)acetyl]-3-(phenylmethyl)-1H-1,4-benzodiazepine, Trifluoroacetate To a stirred mixture of compound D (50 mg, 0.11 mmol) and 2-pyrrlidinone 0.25 mL, 0.33 mmol) in dimethylformamide, was added sodium hydride (14 mg, 0.33 mm) at room temperature under argon. The mixture was allowed to stir at room temperature for 2 h, and poured into a mixture of 1N aqueous hydrochloric acid (75 mL), and ethyl acetate (75 mL). The organic layer was separated, dried (Na$_2$SO$_4$), and concentrated in vacuo. The residue was purified by preparative HPLC (aqueous methanol containing 0.1% trifluoroacetic acid). The product fractions were combined and lyophilized to provide the title compound as a white solid (15 mg, 26%). MS (M+H): 521.

EXAMPLE 5

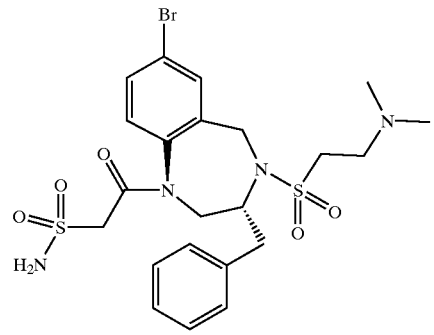

(R)-7-Bromo-4-[[2-(dimethylamino)ethyl]sulfonyl]-2,3,4,5-tetrahydro-b-oxo-3-(phenylmethyl)-1H-1,4-benzodiaze-pine-1-ethanesulfonamide A. (R)-7-Bromo-2,3,4,5-tetrahydro-4-(ethenylsulfonyl)-3-(phenylmethyl)-1H-1,4-benzodiazepine To a stirred solution of the compound B of Example 4 (10 g, 31.5 mmol) in dichloromethane (120 mL) at 0° C., was added dropwise a solution of 2-chloroethanesulfonyl chloride (3.2 mL, 30 mmol) in dichloromethane (10 mL) followed by dropwise addition of DIPEA (5.2 mL, 30 mmol). After stirring for 15 min., 2-chloroethanesulfonyl chloride (1.5 mL, 15 mmol) followed by DIPEA (10.4 mL, 60 mmol) were added. The mixture was allowed to warm to room temperature and poured into water (80 mL). The organic layer was separated, washed with 1N HCl and saturated aqueous NaHCO$_3$ (80 mL each), dried (MgSO$_4$) and concentrated in vacuo to afford the title compound as a yellowish foamy solid (15.2 g). MS (M+H): 406.

17

B. (R)-7-Bromo-2,3,4,5-tetrahydro-4-[[2-(dimethyl-amino) ethyl]sulfonyl]-3-(phenylmethyl)-1H-1,4-benzodiazepine A round bottomed flask was charged with compound A (7 g) and a THF solution of dimethylamine (2 M, 20 mL) at room temperature. The flask was stoppered with a glass stopper and the mixture was allowed to stir for 18 hr. The mixture was concentrated and purified by chromatography (20% acetone in chloroform) to afford title compound (3.25 g, 48% from the compound B of Example 4). MS (M+H): 451.

C. (R)-7-Bromo-4-[[2-(dimethylamino)ethyl]sulfonyl]-2,3, 4,5-tetrahydro-b-oxo-3-(phenylmethyl)-1H-1,4-benzodiazepine-1-ethanesulfonamide To a stirred solution of compound B (90 mg, 0.2 mmol) in dichloromethane (1 mL) at 0° C. under argon, was added chlorosulfonylacetyl chloride (0.063 mL, 0.6 mmol). The mixture was allowed to stir for 8 hr, cooled to −78° C. and liquid ammonia (2 mL) was condensed into the mixture. The stirred mixture was allowed to warm to room temperature over 1 hr, diluted with chloroform (20 mL) and shaken with water (20 mL). The aqueous layer was adjusted to pH 6–7 by careful addition of 1N HCl. The organic layer was separated, dried ($K_2CO_3$), and concentrated. The residue was purified by chromatography (with 10% i-PrOH in chloroform) to afford title compound (51 mg, 44%). MS (M+H): 573.

EXAMPLE 6

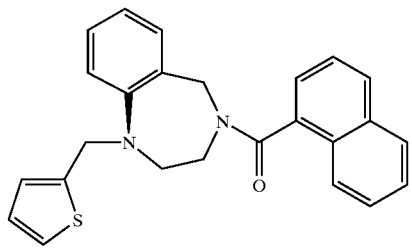

2,3,4,5-Tetrahydro-4-(1-naphthalenylcarbonyl)-1-(2-thienylmethyl)-1H-1,4-benzodiazepine To a stirred solution of the compound C of Example 1 (100 mg, 0.33 mmol), 2-thiophenecarboxaldehyde (56 mg, 0.5 mmol) in a mixture of dichloroethane (2 mL) and acetic acid (1.0 mL), NaBH(OAc)$_3$ (190 mg) was added in one portion. The mixture was stirred for 30 min, and diluted with ethyl acetate (25 mL), followed by NH$_4$OH (3 mL, conc.). The resultant mixture was stirred at room temperature for 18 h and poured into a mixture of ethyl acetate (50 mL) and sat. NaHCO$_3$ (50 mL). This was well shaken. The organic layer was separated, and the aqueous layer was extracted with ethyl acetate (50 mL). The combined organic extracts were dried (MgSO$_4$) and concentrated in vacuo. The residue thus obtained was purified by chromatography (3:1 hexanes and ethyl acetate) to give a solid (40 mg, 30%). MS (M+H): 399.

18

EXAMPLE 7

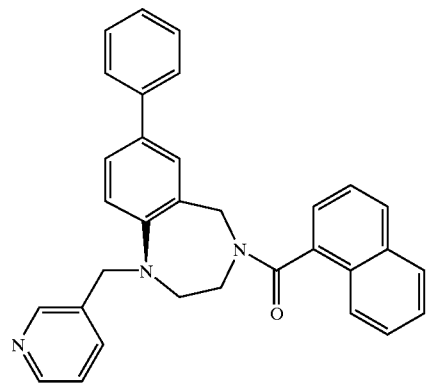

2,3,4,5,-Tetrahydro-4-(1-naphthalenylcarbonyl)-7-phenyl-1-(3-pyridinylmethyl)-1H-1,4-benzodiazepine, hydrochloride The title compound was prepared from nicotinaldehyde and the compound E of Example 2 by following the procedure described for the preparation of Example 6. MS (M+H): 470.

EXAMPLE 8

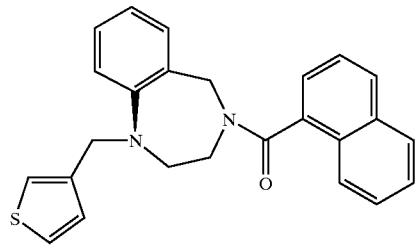

2,3,4,5-Tetrahydro-4-(1-naphthalenylcarbonyl)-1-(3-thienylmethyl)-1H-1,4-benzodiazepine The title compound was prepared from 3-thiophenecarboxaldehyde and the compound C of Example 1 by following the procedure described for the preparation of Example 6. MS (M+H): 475.

EXAMPLE 9

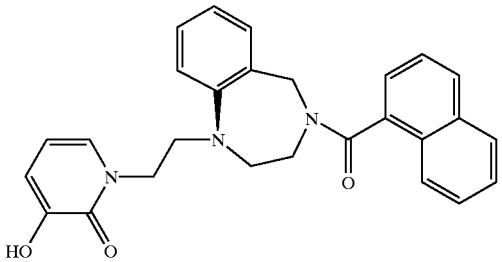

2,3,4,5-Tetrahydro-1-[2-(3-hydroxy-2-oxo-1(2H)-pyridinyl)ethyl]4-(1-naphthalenylcarbonyl)-1H-1,4-benzodiazepine, Dihydrochloride A. Ethyl 3-hydroxy-2-oxo-1(2H)-pyridinylacetate A stirred mixture of 2,3-dihydroxypyridine (11.1 g, 0.10 mol) and ethyl bromoactetate (55.4 mL, 0.5 mol) was refluxed for 12 h, cooled, and concentrated. The residue was recrystallized from ethyl acetate/hexanes to give the title compound as a white solid (19.5 g). MS (M−H) 196.

B. Ethyl 3-[dimethyl-(1,1-dimethyl)ethylsiloxy]-2-oxo-1 (2H)-pyridinylacetate

To a stirred solution of compound A (1.0 g, 5.1 mmol) and imidazole (863 mg, 12.7 mmol) in dimethylformamide (5 mL), was added tert-butyldimethylchlorosilane (920 mg, 6.1 mmol). The resultant solution was allowed to stir for 1 h, and poured into water (100 mL). The aqueous solution was extracted with ethyl acetate. The organic layer was washed with water, 10% aq. lithium chloride, dried (MgSO$_4$), filtered and concentrated to give the title compound as a clear oil (1.5 g). MS (M+H) 312.

C. 3-[Dimethyl-(1,1-dimethyl)ethylsiloxy]-2-oxo-1(2H)-pyridinylethanal.

To a stirred solution of compound B (450 mg, 1.44 mmol) in dry methylene chloride (5 mL) at −78° C., was added diisobutylaluminum hydride (1M in methylene chloride, 2.2 mL, 2.2 mmol) dropwise over 5 min. The mixture was stirred for 1 h at −78° C. and allowed to warm to rt. Water was added and the methylene chloride layer was separated, washed with water, dried (MgSO$_4$), filtered and concentrated to give title compound as a clear oil (385 mg). MS (M+H) 268.

D. 2,3,4,5-Tetrahydro-1-[2-(3-hydroxy-2-oxo-1(2H)-pyridinyl)ethyl]4-(1-naphthalenylcarbonyl)-1H-1,4-benzodiazepine, dihydrochloride The title compound was prepared from compound C and the compound C of Example 1 by following the procedure described for the preparation of Example 6. The product was dissolved in methanol, 1 N HCl in ether was added, and the solvent was removed to give title compound. MS (M+H) 440.

EXAMPLE 10

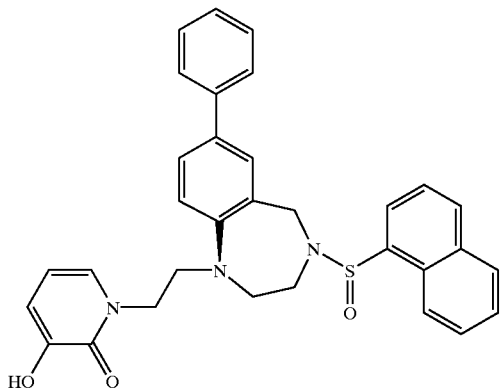

2,3,4,5-Tetrahydro-1-[2-(3-hydroxy-2-oxo-1(2H)-pyridinyl)ethyl]-4-(1-naphthalenylcarbonyl)-7-phenyl-1H-1,4-benzodiazepine, Dihydrochloride The title compound was prepared from the compound C of the Example 9 and the compound E of Example 2 by following the procedure described for the preparation of Example 6. The product was dissolved in methanol, 1 N HCl in ether was added, and the solvent was removed to give title compound. MS (M+H) 516.

EXAMPLE 11

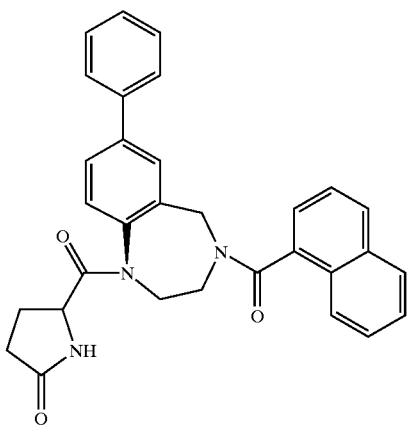

2,3,4,5-Tetrahydro-4-(1-naphthalenylcarbonyl)-1-[(5-oxo-2-pyrrolidinyl)carbonyl]-7-phenyl-1H-1,4-benzodiazepine To a stirred solution of pyroglutamic acid (400 mg, 3.1 mmol) in methylene chloride (6 mL), was added thionyl chloride (4 mL) along with a drop of pyridine at room temperature. The reaction mixture was allowed to stir for 2 h and concentrated. The residue was dissolved in 2 mL methylene chloride. To this stirred solution, was added the compound E of Example 2 (40 mg, 0.106 mmol) and diisopropylethylamine (0.5 mL, 3 mmol) in methylene chloride (5 mL). The mixture was allowed to stir for 16 h, and concentrated. The residue was dissolved in ethyl acetate (50 mL). The resultant solution was washed successively with 1N aqueous potassium bisulfate, saturated aqueous sodium bicarbonate and brine. The organic layer was dried (MgSO$_4$), filtered and concentrated. The residue was purified by preparative HPLC (aqueous methanol with 0.1% TFA) to give 15 mg of the title compound as a white solid. MS (M+NH$_4$): 507.

EXAMPLE 12

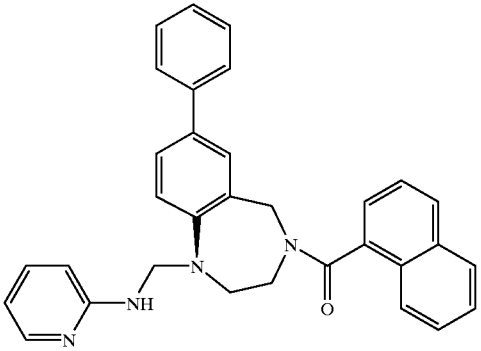

2,3,4,5-Tetrahydro-4-(1-naphthalenylcarbonyl)-7-phenyl-1-[3-(2-pyridinylamino)propyl]-1H-1,4-benzodiazepine, Dihydrochloride A. 3-[Dimethyl(1,1-dimethylethyl)siloxy]-propanol To a stirred solution of 1,3-propanediol (4.8 mL, 66 mmol) in THF (100 mL) was added sodium hydride (60% dispersion in mineral oil, 2.6 g, 66 mmol) followed by tert-butyldimethyl chlorosilane. The solution was allowed to stir for 16 h, and concentrated to an oily residue. Purification by chromatography (40% ethyl acetate in hexanes) afforded title compound (12.3 g). MS (M+H): 191.

B. 3-[Dimethyl(1,1-dimethylethyl)siloxy]-propanal

To a stirred solution of oxalyl chloride (504 mg, 4 mmol) in 20 mL methylene chloride at −63° C. under argon, was added dimethyl sulfoxide (1.0 g, 2.6 mmol) in methylene chloride (5 mL). This was followed by addition of the compound A (1.0 g, 2.6 mmol) in methylene chloride (5 mL) over 15 min keeping the reaction temperature below −50° C. The resultant solution was stirred for 30 min at −63° C., then a solution of triethylamine (1.2 g, 11.9 mmol) in methylene chloride (5 mL) was added over 15 min keeping the solution below −50° C. The reaction was allowed to stir for 30 min, and quenched by addition of 1M potassium hydrogen sulfate (4.5 mL), water (20 mL) and ethyl ether (200 mL). The layers were separated and the aqueous layer was made basic using saturated aqueous sodium bicarbonate and extracted with ethyl acetate (3×50 mL). The combined organic layers were dried (MgSO$_4$) and concentrated to yield title compound (1.0 g). MS (M+H): 189.

C. 2,3,4,5-Tetrahydro-4-(1-naphthalenylcarbonyl)-7-phenyl-1-[3-Dimethyl(1,1-dimethylethyl)siloxypropyl]-1H-1,4-benzodiazepine The title compound was prepared from compound B and the compound E of Example 2 by following the procedure described for the preparation of Example 6. MS (M+H) 552.

D. 2,3,4,5-Tetrahydro4-(1-naphthalenylcarbonyl)-7-phenyl-1-[3-hydroxypropyl]-1H-1,4-benzodiazepine A solution of compound C (300 mg, 0.54 mmol) in dioxane (6 mL) and 4 N aqueous HCl solution was stirred for 1 h and concentrated. The residue was triturated with diethyl ether to give 230 mg of title compound as a white solid. MS (M+H): 437.

E. 2,3,4,5-Tetrahydro-4-(1-naphthalenylcarbonyl)-7-phenyl-1-[3-(2-pyridinylamino)propyl]-1H-1,4-benzodiazepine, Dihydrochloride To a stirred solution of compound D (50 mg, 0.11 mmol) in dry methylene chloride (5 mL) at −40° C, was added di-(tert-butyl)-methylpyridine (23 mg, 0.11 mmol) followed by triflic anhydride (0.19 mL, 0.11 mmol). The solution stirred for 30 min at −40° C. and 2-aminopyridine (16 mg, 0.17 mmol) was added. The mixture was allowed to stir at 40° C. for 30 min and warmed to room temperature over 2 h. The reaction was concentrated and purified by preparative HPLC (aqueous methanol with 0.1% TFA). The product was dissolved in methanol, 1 N HCl in ether was added, and the solvent was removed to give the title compound as a solid (20 mg). MS (M+H): 513.

EXAMPLE 13

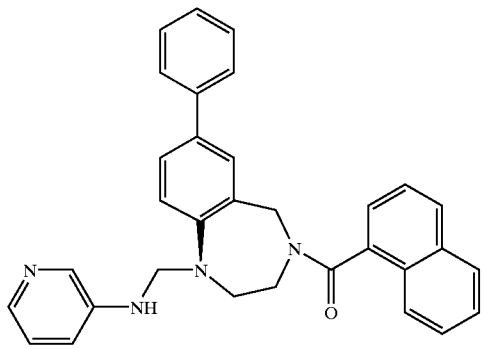

2,3,4,5-Tetrahydro-4-(1-naphthalenylcarbonyl)-7-phenyl-1-[3-(3-pyridinylamino)propyl]-1-1,4-benzodiazepine, Dihydrochloride The title compound was prepared by following the procedure described for the preparation of Example 12 except 3-aminopyridine was used in the place of 2-aminopyridine. MS (M+H): 513.

EXAMPLE 14

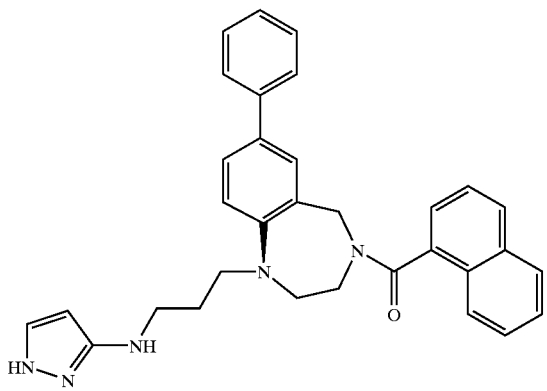

2,3,4,5-Tetrahydro-4-(1-naphthalenylcarbonyl)-7-phenyl-1-[3-(1H-pyrazol-3-ylamino)propyl]-1H-1,4-benzodiazepine, Dihydrochloride The title compound was prepared by following the procedure described for the preparation of Example 12 except 3-aminopyrazole was used in the place of 2-aminopyridine. MS (M+H): 502.

EXAMPLE 15

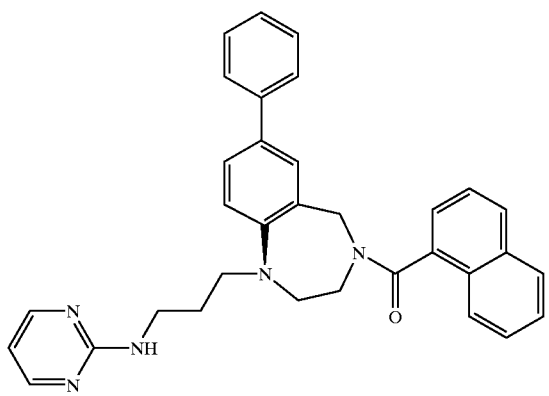

2,3,4,5-Tetrahydro-4-(1-naphthalenylcarbonyl)-7-phenyl-1-[3-(2-pyrimidinylamino)propyl]-1H-1,4-benzodiazepine, Dihydrochloride The title compound was prepared by following the procedure described for the preparation of Example 12 except 2-aminopyrimidine was used in the place of 2-aminopyridine. MS (M+H): 514.

EXAMPLE 16

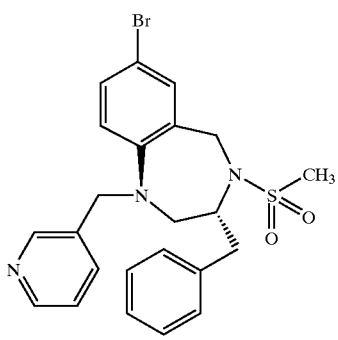

(R)-7-Bromo-2,3,4,5-tetrahydro-4-(methylsulfonyl)-
1-(3-pyridinylmethyl)-3-(phenylmethyl)-1H-1,4-
benzodiazepine, Hydrochloride The title compound was prepared from the compound C of Example 4 and nicotinaldehyde by following the procedure for the preparation of Example 6. MS (M+H): 486.

EXAMPLE 17

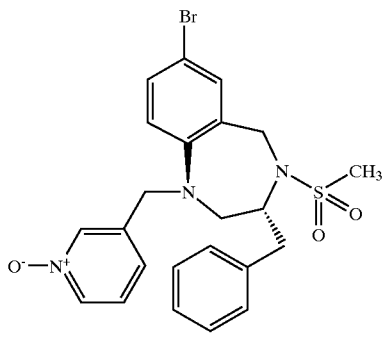

(R)-7-Bromo-2,3,4,5-tetrahydro-4-(methylsulfonyl)-
1-(1-oxo-3-pyridinylmethyl)-3-(phenylmethyl)-1H-
1,4-benzodiazepine, Hydrochloride To a stirred solution of Example 16 (25 mg, 0.05 mmol) in methylene chloride in the presence of sodium bicarbonate was added mCPBA (50 mg) at 0° C. The mixture was stirred for 3 h, and treated with aq. potassium carbonate. The suspension was stirred, filtered, and concentrated. The residue was dissolved in methanol, 1N HCl in ether was added, solvent was removed to give title compound as a solid (22 mg). MS (M+H): 502.

EXAMPLE 18

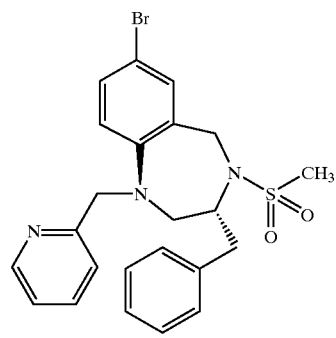

(R)-7-Bromo-2,3,4,5-tetrahydro-4-(methylsulfonyl)-
1-(2-pyridinylmethyl)-3-(phenylmethyl)-1H-1,4-
benzodiazepine, hydrochloride.

The title compound was prepared from the compound C of Example 4 and 2-pyridylcarboxaldehyde by following the procedure for the preparation of Example 6. MS (M+H): 486.

EXAMPLE 19

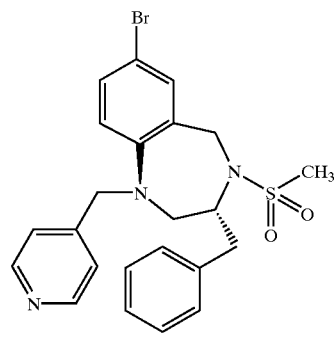

(R)-7-Bromo-2,3,4,5-tetrahydro-4-(methylsulfonyl)-
1-(4-pyridinylmethyl)-3-(phenylmethyl)-1H-1,4-
benzodiazepine, Hydrochloride The title compound was prepared from the compound C of Example 4 and 4-pridylcarboxaldehyde by following the procedure for the preparation of Example 6. (M+H): 486.

EXAMPLE 20

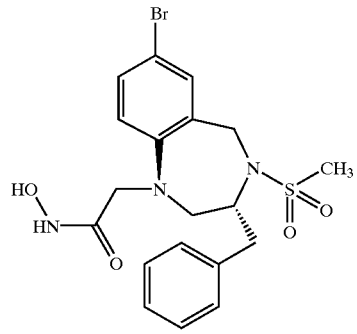

(R)-7-Bromo-2,3,4,5-tetrahydro-N-hydroxy-4-
(methylsulfonyl)-1H-1,4-benzodiazepine-1-
acetamide, Hydrochloride A. Ethyl (R)-7-Bromo-2,3,4,5-tetrahydro-4-(methylsulfonyl)-1-1,4-benzodiazepine-1-acetate The title compound was prepared from the compound C of Example 4 and ethyl glyoxalate by following the procedure for the preparation of Example 6. MS (M+H): 481.

B. (R)-7-Bromo-2,3,4,5-tetrahydro-4-(methylsulfonyl)-1H-1,4-benzodiazepine-1-acetic Acid To a stirred solution of compound A (480 mg, 1.0 mmol) in THF in the presence of aq. methanol, was added LiOH-H₂O (210 mg, 5.0 mmol). The mixture was allowed to stir for 3 h, and made acidic with 1 N HCl solution. The mixture was concentrated in vacuo, and partitioned between ethyl acetate and 1 N HCl solution. The organic layer was separated, dried, and concentrated to give the title compound (400 mg, 89%). MS (M−H): 451.

C. (R)-7-Bromo-2,3,4,5-tetrahydro-N-hydroxy-4-(methylsulfonyl)-1H-1,4-benzodiazepine-1-acetamide, Hydrochloride To a stirred solution of compound B (230 mg, 0.5 mmol) in DMF, was added hydroxylamine hydrochloride (350 mg, 5.0 mmol), triethylamine (0.07 mL, 0.5 mmol), and 1-(3-dimethylaminopropyl)-3-ethylcarbodiimide hydrochloride (100 mg, 0.5 mmol). The mixture was allowed to stir for 18 h, and concentrated in vacuo. The residue was partitioned between ethyl acetate and 1 N HCl solution. The organic layer was separated, dried, concentrated. The residue was purified by chromatography (1:1; ethyl acetate, hexanes). The resultant oil was dissolved in methanol, 1 N HCl was added, the solvent was removed to give title compound. MS (M+H): 468.

EXAMPLE 21

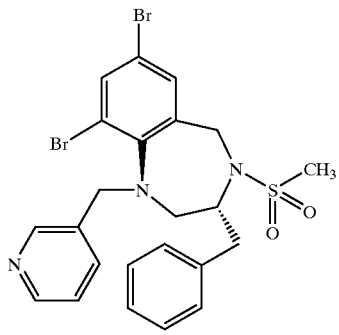

(R)-7,9-Dibromo-2,3,4,5-tetrahydro-4-(methylsulfonyl)-1-(3-pyridinylmethyl)-3-(phenylmethyl)-1H-1,4-benzodiazepine, Hydrochloride To a stirred solution of the compound (200 mg) of Example 16 in methanol and water (7.5 mL/0.5 mL), was added N-bromosuccinimide (73 mg). The mixture was allowed to stir for 1 h, and solvent was removed. The residue was purified by silica gel column chromatography (ethyl acetate/hexanes) to give a solid (90 mg, 35%). (M+H): 564.

EXAMPLE 22

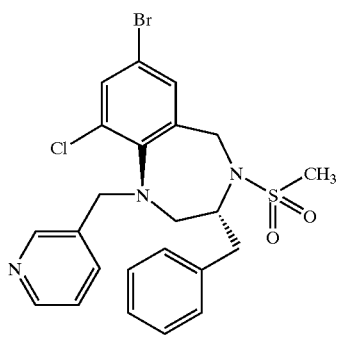

(R)-7-Bromo-9-chloro-2,3,4,5-tetrahydro-4-(methylsulfonyl)-1-(3-pyridinylmethyl)-3-(phenylmethyl)-1H-1,4-benzodiazepine, Hydrochloride The title compound was prepared by following the same procedure employed as the preparation of Example 21, except N-chlorosuccinimide was used in the place of N-bromosuccinimide. (M+H): 520.

EXAMPLE 23

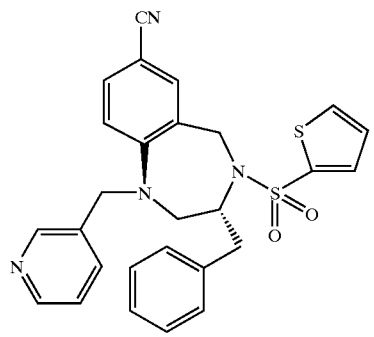

(R)-7-Cyano-2,3,4,5-tetrahydro-3-(phenylmethyl)-1-(3-pyridinylmethyl)-4-(2-thienesulfonyl)-1H-1,4-benzodiazepine, Hydrochloride A. (R)-7-Cyano-2,3,4,5-tetrahydro-3-phenylmethyl-benzodiazapine To a stirred solution of compound B (10 g, 31.5 mmol) of Example 4 in N-methylpyrrolidinone, was added copper cyanide (8.5 g). This was heated at 200° C. for 4 h. The mixture was poured into aqueous ethylene diamine solution at 0° C. The precipitate was collected, and washed with 10% NH₄OH solution. This was triturated with hot ethyl acetate (3×100 mL). The combined ethyl acetate solution was dried, concentrated to give an oil (8.0 g).

B. (R)-7-Cyano-2,3,4,5-tetrahydro-3-phenylmethyl-4-(2-thienesulfonyl)-benzodiazapine To a stirred solution of compound A (6 g, 22.8 mmol), diisopropylethylamine (10 mL, 57 mmol) in CH₂Cl₂ (150 mL), was added 2-thiophenesulfonyl chloride (5 g, 27 mmol) in CH₂Cl₂ (5 mL) at 0° C. The solution was stirred at 0° C. for 10 min., at room temperature for 10 hrs. The solution was diluted with CH₂Cl₂ (100 mL) and washed with 2.5% NaOH (100 mL), followed by NaCl (sat., 150 mL). The solution was dried over Na₂SO₄, evaporated and purified by flash chromatography (20% EtOAc in hexane and 40% EtOAc in hexane) to provide a yellow solid (7.8 g).

C. (R)-7-Cyano-2,3,4,5-tetrahydro-3-(phenylmethyl)-1-(3-pyridinylmethyl)-4-(2-thienesulfonyl)-1H-1,4-benzodiazepine, Hydrochloride The title compound was prepared from the compound B and nicotinaldehyde by following the procedure for the preparation of Example 6. MS (M+H): 501.

EXAMPLE 24

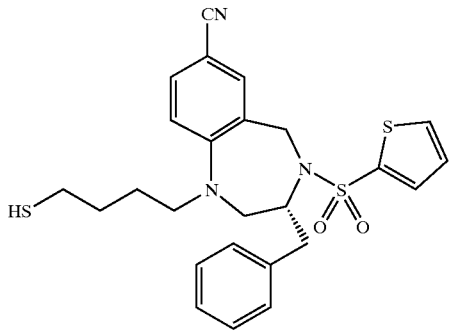

(R)-7-Cyano-2,3,4,5-tetrahydro-1-(4-butylthio)-3-(phenylmethyl)-4-(2-thienylsulfonyl)-1H-1,4-benzodiazepine A. (R)-7-Cyano-2,3,4,5-tetrahydro-1-(4-chlorobutyl)-3-(phenylmethyl)-4-(2-thienylsulfonyl)-1H-1,4-benzodiazepine To a solution of Compound B of Example 23 (410 mg, 1 mmol) dissolved in $CH_2Cl_2$ (10 mL) was added 2(chloropropyl)-1,3-dioxolane(0.53 mL, 4 mmol) followed by trifluoroacetic acid (10 mL) and triethylsilane (0.64 mL, 4 mmol). Stirring was continued for 1 hr and the solvent was removed under vacuum. The residue was neutralized with saturated aqueous $Na_2CO_3$, diluted with $CH_2Cl_2$, washed with brine and evaporated to a yellow solid (500 mg).

B. (R)-7-Cyano-2,3,4,5-tetrahydro-1-(4-butyl-thioamidino)-3-(phenylmethyl)-4-(2-thienylsulfonyl)-1H-1,4-benzodiazepine To a solution of Compound A (500 mg, 1 mmol) in ethanol (15 mL) was added thiourea (400 mg, 5.26 mmol). The stirring at reflux for 4 days, the reaction was cooled and used in the next step. (yield 500 mg). MS (M+H) 540.

C. (R)-7-Cyano-2,3,4,5-tetrahydro-1-(4-butylthio)-3-(phenylmethyl)4-(2-thienylsulfonyl)-1H-1,4-benzodiazepine To a solution of Compound B was added morpholine (1 mL) and the solution was heated to 78° C. for 2 hrs. On cooling to RT, the solution was diluted with $CH_2Cl_2$, washed with water, brine, dried ($MgSO_4$) filtered and concentrated under vacuum. The residue was purified using a flash column (0–40% ethyl acetate/hexane) to provide a light yellow solid. Treatment with 1N aqueous HCl followed by concentration under vacuum provided the hydrochloride salt of the title compound as a light yellow solid. (Yield; 240 mg). MS (M+H) 498.

EXAMPLE 25

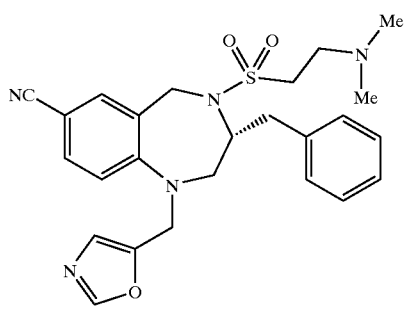

(R)-7-Cyano-4-[[2-(dimethylamino)ethyl]sulfonyl]-2,3,4,5-tetrahydro-1-(5-oxazolylmethyl)-3-(phenylmethyl)-1H-1,4-benzodiazepine A. (R)-7-Cyano-2,3,4,5-tetrahydro4-(ethenylsulfonyl)-3-(phenylmethyl)-1H-1,4-benzodiazepine The title compound was prepared from Compound A of Example 23 following the procedure of Compound A of Example 5.

B. (R)-7-Cyano-2,3,4,5-tetrahydro4-[[2-(dimethyl-amino)ethyl]sulfonyl]-3-(phenylmethyl)-1H-1,4-benzodiazepine The title compound was prepared from Compound A following the procedure of Compound B of Example 5.

C. (R)-7-Cyano-4-[[2-(dimethylamino)ethyl]sulfonyl]-2,3,4,5-tetrahydro-1-(5-oxazolylmethyl)-3-(phenylmethyl)-1H-1,4-benzodiazepine To a mixture of 4-formyloxazole diethylacetal (68.4 mg, 0.4 mmol) and Compound B (80 mg, 0.2 mmol) in 1,2-dichloroethane (0.5 mL) at rt was added TFA (0.2 mL), followed by triethylsilane (0.1 mL). The resulting mixture was stirred at rt for 10 hours and neutrallized with $NaHCO_3$ solution. It was extracted with DCM (2×10 mL). The combined extract solution was dried over $Na_2SO_4$ and concentrated. The residue was purified by preparative HPLC (column: YMC OD S5 20×100 mm; flow rate: 20 mL/min; UV: 220 nm; solvents: linear gradient from 10 to 90% MeOH in water containing 0.1% TFA.). Those fractions containing the desired product were pooled and concentrated to afford the product, which was converted to hydrochloric acid salt of the title compound, 67 mg (65%). MS: m/e (M+H)+=480.

EXAMPLE 26

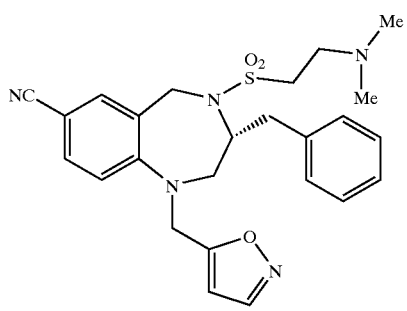

(R)-7-Cyano-4-[[2-(dimethylamino)ethyl]sulfonyl]-2,3,4,5-tetrahydro-1-(5-isoxazolylmethyl)-3-(phenylmethyl)-1H-1,4-benzodiazepine To a mixture of 3-formylisoxazole (19.4 mg, 0.2 mmol) and Compound B of Example 25 (39.9 mg, 0.1 mmol) in DCM (0.5 mL) at rt was added TFA (45 mg, 0.4 mmol), followed by triethylsilane (35 mg, 0.3 mmol). The resulting mixture was stirred at rt for 1 hour, neutrallized with NaHCO$_3$ solution and extracted with DCM (2×5 mL). The combined extract was dried over Na$_2$SO$_4$ and concentrated. The residue was purified by flash column chromatography (SiO$_2$; ethyl acetate: methanol ammonia/100:10:0.1) to afford the title compound, 45 mg (87%). MS: m/e (M+H)$^+$= 480.

EXAMPLE 27

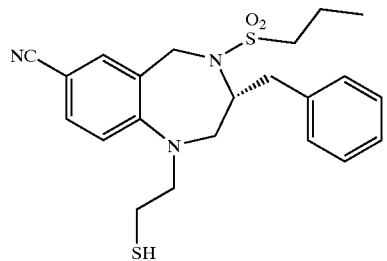

(R)-7-Cyano-2,3,4,5-tetrahydro-1-(2-mercaptoethyl)-3-(phenylmethyl)-4-(propylsulfonyl)-1H-1,4-benzodiazepine A. (R)-7-Cyano-2,3,4,5-tetrahydro-4-(propylsulfonyl)-3-(phenylmethyl)-1H-1,4-benzodiazepine The title compound was prepared by reaction of Compound A of Example 23 with 1-propanesulfonylchloride following the procedure of Compound B of Example 23.

B. (R)-7-Cyano-2,3,4,5-tetrahydro-1-(2-bromoethyl)-3-(phenylmethyl)-4-(propylsulfonyl)-1H-1,4-benzodiazepine The title compound was prepared by stirring Compound A (957 mg, 2.6 mmol) and bromoacetaldehyde dimethyl acetal (0.70 mL, 6 mmol) at room temperature for 24 hours. Concentration in vacuo followed by flash chromatography on silica gel (30% EtOAC/hexane eluent) afforded the desired material as a white solid, 1.1 g (89%).

C. (R)-7-Cyano-2,3,4,5-tetrahydro-1-(2-(triphenylmethyl) mercaptoethyl)-3-(phenylmethyl)-4-(propylsulfonyl)-1H-1, 4-benzodiazepine To a solution of Compound B (476 mg, 1 mmol) in DMF (5 mL) was added potassium carbonate (276 mg, 2 mmol) under argon at rt, followed by triphenylmethane mercaptan (290 mg, 1.05 mmol). The mixture was stirred vigorously for 20 hours. Water (20 mL) and ethyl acetate (20 mL) were added and the organic layer was separated. The ethyl acatate solution was washed with brine (20 mL), dried (MgSO$_4$) and concentrated. The residue was purified by flash silica gel column eluting with 20% ethyl acetate in hexanes to afford white solid, 670 mg (100%).

D. (R)-7-Cyano-2,3,4,5-tetrahydro-1-(2-mercaptoethyl)-3-(phenylmethyl)-4-(propylsulfonyl)-1H-1,4-benzodiazepine To a solution of Compound C (220 mg, 0.33 mmol) and triethylsilane (0.2 mL) in DCM (1 mL) was added TFA (0.2 mL) at rt. under argon. The mixture was stirred at rt for 0.5 hour and concentrated. The residue was purified by flash column chromatography (SiO$_2$; hexanes:ethyl acetate/3:1) to afford the title compound as a foam, 85 mg (60%) MS m/e (M+H)$^+$=430.

EXAMPLE 28

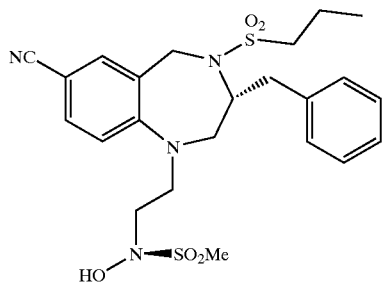

(R)-N-[2-[7-Cyano-2,3,4,5-tetrahydro-3-(phenylmethyl)-4-(propylsulfonyl)-1H-1,4-benzodiazepin-1-yl]ethyl]-N-hydroxymethanesulfonamide A. (R)-N-[2-[7-Cyano-2,3,4,5-tetrahydro-3-(phenylmethyl)-4-(propylsulfonyl)-1-1,4-benzodiazepin-1-yl]ethyl]-N-[(4-methoxyphenyl)methoxy] methanesulfonamide A mixture of Compound B of Example 27 (47.6 mg, 0.1 mmol), N-[(4-methoxyphenyl)methoxy]methanesulfamide (25 mg, 0.11 mmol) and potassium carbonate (100 mg, 0.72 mmol) was stirred in DMF (0.5 mL) at rt for 3 hours. Water (10 mL) was added and the precipitate was collected. The solids were washed with water and dried in vacuum to afford the title compound (60.5 mg, 96%).

B. (R)-N-[2-[7-Cyano-2,3,4,5-tetrahydro-3-(phenylmethyl)-4-(propylsulfonyl)-1H-1,4-benzodiazepin-1-yl]ethyl]-N-hydroxymethanesulfonamide Compound A (58 mg, 0.093 mmol) was dissolved in TFA (0.2 mL) and stirred at rt for 2 hours. The reaction mixture was concentrated and the residue was purified by flash column (silica gel; hexanes:ethyl acetate/2:1) to afford the title compound as a foam, 23 mg (49%) MS m/e (M+H)$^+$= 507; (M-H)$^-$=505.

EXAMPLE 29

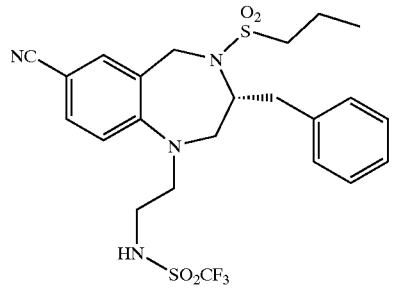

(R)-N-[2-[7-Cyano-2,3,4,5-tetrahydro-3-(phenylmethyl)-4-(propylsulfonyl)-1H-1,4-benzodiazepin-1-yl]ethyl] trifluoromethanesulfonamide A. (R)-1-(2-Azidoethyl)-7-cyano-2,3,4,5-tetrahydro-3-(phenylmethyl)-4-(propylsulfonyl)-1H-1,4-benzodiazepine A mixture of Compound B of Example 27 (95.2 mg, 0.2 mmol) and sodium azide (15 mg, 0.23 mmol) in DMF (0.5 mL) was stirred at 70° C. overnight. The mixture was cooled to rt and diluted with water. The solid was collected, washed with water and dried to afford the title compound, 83 mg (95%) LC/MS: m/e (M+H)$^+$=439.

B. (R)-1-(2-Aminoethyl)-7-cyano-2,3,4,5-tetrahydro-3-(phenylmethyl)-4-(propylsulfonyl)-1H-1,4-benzodiazepine A solution of Compound A (80 mg, 0.18 mmol) in MeOH (3 mL) was hydrogenated under hydrogen atmosphere in the presence of catalytic amount of Pd/C (10%) for 10 min. The mixture was filtered and the filtrate was concentrated to afford the title compound as a gel, 53 mg (71%) LC/MS: m/e (M+H)$^+$=413.

C. (R)-N-[2-[7-Cyano-2,3,4,5-tetrahydro-3-(phenylmethyl)-4-(propylsulfonyl)-1H-1,4-benzodiazepin-1-yl]ethyl]trifluoromethanesulfonamide To a solution of Compound B (30 mg, 0.073 mmol) and triethylamine (0.015 mL) in DCM (0.5 mL) at −78° C. was added triflic anhydride (22.6 mg, 0.08 mmol) dropwise. The mixture was stirred at −78° C. for 0.5 hour and then warmed up to rt. The reaction mixture was washed with water and concentrated. The residue was purified by preparative HPLC (YMC S5 ODS 100×20 mm; 40–90% MeOH in water containing 0.2% TFA; 20 mL/min; UV 220 nm) to afford the title compound as a colorless solid, 14 mg (35%) MS m/e (M+H)$^+$=545; (M−H)$^-$=543.

EXAMPLE 30

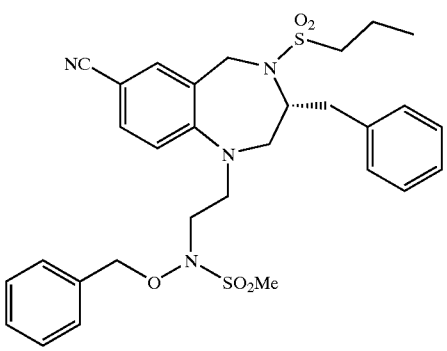

(R)-N-[2-[7-Cyano-2,3,4,5-tetrahydro-3-(phenylmethyl)-4-(propylsulfonyl)-1H-1,4-benzodiazepin-1-yl]ethyl]-N(phenylmethoxy)methanesulfonamide A mixture of Compound B of Example 27 (95.2 mg, 0.2 mmol) and N-phenylmethoxyl methanesulfamide (44 mg, 0.22 mmol) was stirred with potassium carbonate (69 mg, 0.5 mmol) in DMF (1 mL) at 70–80° C. for 2 hours. Water (10 mL) was added and the precipitates were collected. The solids were dried in vacuo and redissolved in DCM. The DCM solution was filtered and the filtrate solution was concentrated to afford the title compound as a colorless foam, 119.0 mg (100%) MS m/e 597 (M+H)$^+$.

EXAMPLE 31

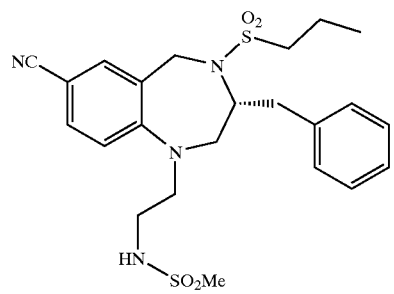

(R)-N-[2-[7-Cyano-2,3,4,5-tetrahydro-3-(phenylmethyl)-4-(propylsulfonyl)-1H-1,4-benzodiazepin-1-yl]ethyl]methanesulfonamide Methanesulfonamide (23.8 mg, 0.25 mmol) was added to a suspension of sodium hydride (10 mg, 0.25 mmol, 60% in oil, washed with hexanes) in THF (1.5 mL). The mixture was stirred at rt for 30 min. and Compound B of Example 27 (47.6 mg, 0.1 mmol) was added. The resulting mixture was stirred at reflux temperature for 16 hours. The reaction mixture was cooled to rt, diluted with DCM (10 mL) and washed with water. The DCM solution was dried over Na$_2$SO$_4$ and concentrated. The residue was purified by preparative HPLC (Column: YMC S-5 ODS 100×20 mm; UV: 220 nm; Flow rate: 20 mL/min; solvent: gradient from 50–90% MeOH in water containing 0.1% TFA in 10 min.). The fractions containing the desired products were pooled and concentrated to afford the title compound as a colorless foam, 5.2 mg (10.6%) MS m/e 491 (M+H)$^+$; 489(M−H)$^-$.

EXAMPLE 32

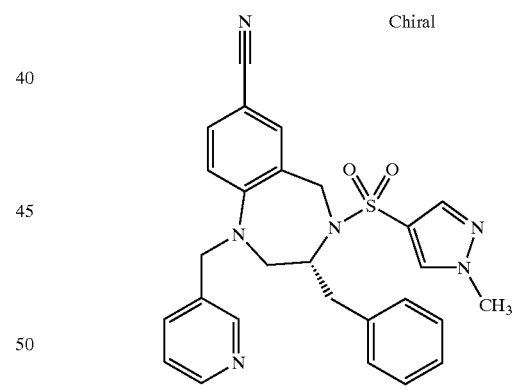

(3R)-2,3,4,5-Tetrahydro-4-[(1-methyl-1H-pyrazol-4-yl)sulfonyl]-3-(phenylmethyl)-1-(3-pyridinylmethyl)-1H-1,4-benzodiazepine-7-carbonitrile A. (3R)-2,3,4,5-Tetrahydro-4-[(1-methyl-1H-pyrazol-4-yl)sulfonyl]-3-(phenylmethyl)-1H-1,4-benzodiazepine-7-carbonitrile The title compound was prepared from Compound A of Example 23 and 1-methyl-1H-pyrazole-4-sulfonyl chloride following the procedure of Compound B of Example 23.

B. (3R)-2,3,4,5-Tetrahydro-4-[(1-methyl-1H-pyrazol-4-yl)sulfonyl]-3-(phenylmethyl)-1-(3-pyridinylmethyl)-1H-1,4-benzodiazepine-7-carbonitrile The title compound was prepared from Compound A using the procedure of Compound C of Example 23.

MS: (M+H)$^+$499; Elemental analysis for C$_{27}$H$_{26}$N$_6$O$_2$S.1.17HCl1.20H$_2$O; Calc: C, 57.61 H, 5.30; N, 14.93; S, 5.70; Cl, 7.37; Found: C, 57.62; H, 5.15; N, 14.85; S, 5.47; Cl, 7.39.

EXAMPLE 33

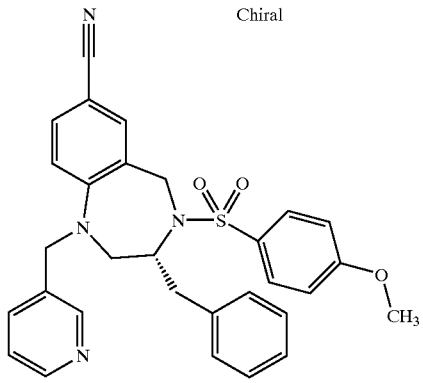

(3R)-2,3,4,5-Tetrahydro4-[(4-methoxyphenyl)sulfonyl]-3-(phenylmethyl)-1-(3-pyridinylmethyl)-1H-1,4-benzodiazepine-7-carbonitrile A. (3R)-2,3,4,5-Tetrahydro-4-[(4-methoxyphenyl)sulfonyl]-3-(phenylmethyl)-1H-1,4-benzodiazepine-7-carbonitrile The title compound was prepared from Compound A of Example 23 and 4-methoxyphenylsulfonyl chloride following the procedure of Compound B of Example 23.

B. (3R)-2,3,4,5-Tetrahydro-4-[(4-methoxyphenyl)sulfonyl]-3-(phenylmethyl)-1-(3-pyridinylmethyl)-1H-1,4-benzodiazepine-7-carbonitrile The title compound was prepared from Compound A using the procedure of Compound C of Example 23.

MS: (M+H)$^+$525; Elemental analysis for C$_{30}$H$_{28}$N$_4$O$_3$S.1.05HCl1.21H$_2$O; Calc: C, 61.62 H, 5.43; N, 9.58; S, 5.48; Cl, 6.37; Found: C, 61.63; H, 5.29; N, 9.51; S, 5.23; Cl, 6.38.

EXAMPLE 34

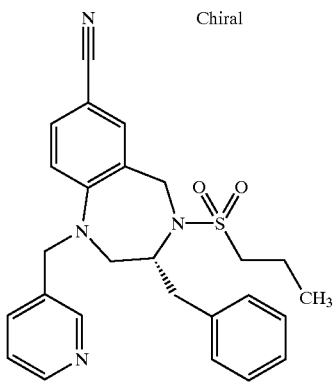

(3R)-2,3,4,5-Tetrahydro-3-(phenylmethyl)-4-(propylsulfonyl)-1-(3-pyridinylmethyl)-1H-1,4-benzodiazepine-7-carbonitrile A. (3R)-2,3,4,5-Tetrahydro-3-(phenylmethyl)4-(propylsulfonyl)-1-1,4-benzodiazepine-7-carbonitrile The title compound was prepared from Compound A of Example 23 and propanesulfonyl chloride following the procedure of Compound B of Example 23.

B. (3R)-2,3,4,5-Tetrahydro-3-(phenylmethyl)-4-(propylsulfonyl)-1-(3-pyridinylmethyl)-1H-1,4-benzodiazepine-7-carbonitrile The title compound was prepared from Compound A using the procedure of Compound C of Example 23.

MS: (M+H)$^+$461; Elemental analysis for C$_{26}$H$_{28}$N$_4$O$_2$S.1.05HCl0.50H$_2$O; Calc: C, 61.49 H, 5.96; N, 11.03; S, 6.31; Cl, 7.33; Found: C, 61.49; H, 6.07; N, 10.91; S, 6.17; Cl, 7.33.

EXAMPLE 35

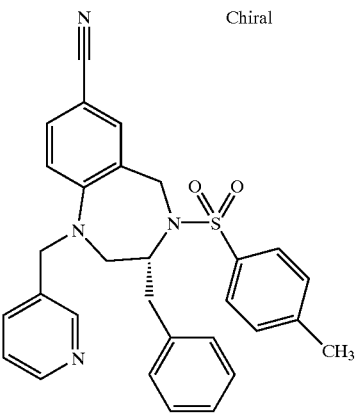

(3R)-2,3,4,5-Tetrahydro-4-[(4-methylphenyl)sulfonyl]-3-(phenylmethyl)-1-(3-pyridinylmethyl)-1H-1,4-benzodiazepine-7-carbonitrile A. (3R)-2,3,4,5-Tetrahydro-4-[(4-methylphenyl)sulfonyl]-3-(phenylmethyl)-1H-1,4-benzodiazepine-7-carbonitrile The title compound was prepared from Compound A of Example 23 and toluenesulfonyl chloride following the procedure of Compound B of Example 23.

B. (3R)-2,3,4,5-Tetrahydro-4-[(4-methylphenyl)sulfonyl]-3-(phenylmethyl)-1-(3-pyridinylmethyl)-1H-1,4-benzodiazepine-7-carbonitrile The title compound was prepared from Compound A using the procedure of Compound C of Example 23.

MS: (M+H)$^+$509; Elemental analysis for C$_{30}$H$_{28}$N$_4$O$_2$S.1.0HC1.15H$_2$O; Calc: C, 63.68 H, 5.58; N, 9.90; S, 5.67; Cl, 6.27; Found: C, 63.69; H, 5.65; N, 9.71; S, 5.63; Cl, 6.05.

EXAMPLE 36

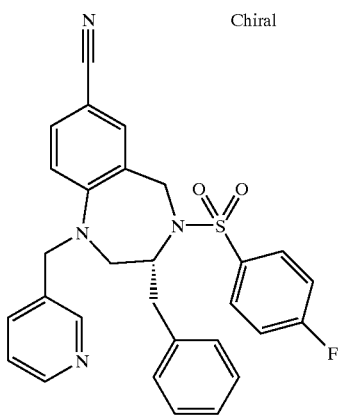

(3R)-4-[(4-Fluorophenyl)sulfonyl]-2,3,4,5-tetrahydro-3-(phenylmethyl)-1-(3-pyridinylmethyl)-1H-1,4-benzodiazepine-7-carbonitrile A. (3R)-4-[(4-Fluorophenyl)sulfonyl]-2,3,4,5-tetrahydro-3-(phenylmethyl)-1H-1,4-benzodiazepine-7-carbonitrile The title compound was prepared from Compound A of Example 23 and 4-fluorophenylsulfonyl chloride following the procedure of Compound B of Example 23.

B. (3R)-4-[(4-Fluorophenyl)sulfonyl]-2,3,4,5-tetrahydro-3-(phenylmethyl)-1-(3-pyridinylmethyl)-1H-1,4-benzodiazepine-7-carbonitrile The title compound was prepared from Compound A using the procedure of Compound C of Example 23.

MS: (M+H)$^+$513; Elemental analysis for $C_{29}H_{25}N_4O_2SF.1.0HCl0.70H_2O$; Calc: C, 62.01 H, 4.92; N, 9.97; S, 5.71; Cl, 6.31; F, 3.38; Found: C, 62.01; H, 5.13; N, 9.61; S, 5.65; Cl, 6.02; F, 3.66.

EXAMPLE 37

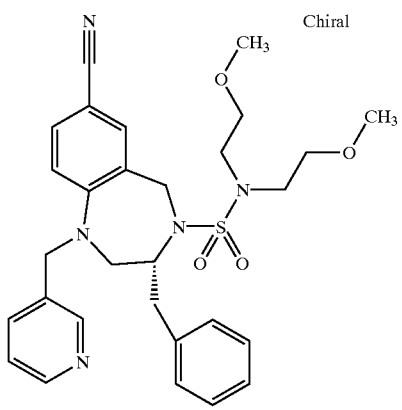

(3-pyridinylmethyl)-4H-1,4-benzodiazepine-4-sulfonamide

A. N,N-bis(2-methoxyethyl)sulfamyl Chloride

A premixed solution of bis-methoxyethylamine (15.0 ml, 102 mmol, 1.00 equiv.) and triethylamine (21.3 ml, 153 mmol, 1.50 equiv.) was added dropwise to a solution of sulfuryl chloride (20.7 ml, 153 mmol, 1.50 equiv.) in $CH_2Cl_2$ at 0° C. The reaction mixture was continued stirred at 0° C. for 2 h, poured into ice and extracted with $CH_2Cl_2$ (3×100 ml). The combined organic extracts were washed with a saturated NaCl soln (1×100 ml), the organic layer dried ($Na_2SO_4$), filtered and concentrated under vacuum to afford the title compound (18.5 g, 80%) which was used without further purification. $^1$HNMR ($CDCl_3$): 3.37 (s, 6H), 3.64–3.64 (m, 8H)

B. (3R)-7-Cyano-1,2,3,5-tetrahydro-N,N-bis(2-methoxyethyl)-3-(phenylmethyl)-4H-1,4-benzodiazepine-4-sulfonamide Compound A (0.484 g, 2.09 mmol, 1.10 equiv) was added to a solution of Compound A of Example 23 (0.500 g, 1.90 mmol, 1.00 equiv) and DIPEA (0.661 ml, 3.80 mmol, 2.00 equiv) in acetonitrile (10.0 ml) and the reaction mixture was heated at 65° C. for 7 hours. The reaction mixture was cooled to room temperature, quenched with 1N NaOH (50.0 ml) and the solution was extracted with $CH_2Cl_2$ (3×70 ml). The combined organic extracts were dried ($Na_2SO_4$), filtered and concentrated under vacuum. The residue was purified by silica gel flash chromatography (eluting 1/1 ethyl acetate/hexane), the appropriate fractions were isolated and concentrated under vacuum to afford the title compound (0.670 g, 77%)as a glassy solid. MS: (M–H)$^-$457.

C. (3R)-7-Cyano-1,2,3,5-tetrahydro-N,N-bis(2-methoxyethyl)-3-(phenylmethyl)-1-(3-pyridinylmethyl)-4H-1,4-benzodiazepine-4-sulfonamide The title compound was prepared from Compound B using the procedure of Compound C of Example 23.

HRMS (M+H)+; Calc: 550.2458; Found: 550.2474 (–2.5/–1.4) ppm/mmu.

EXAMPLE 38

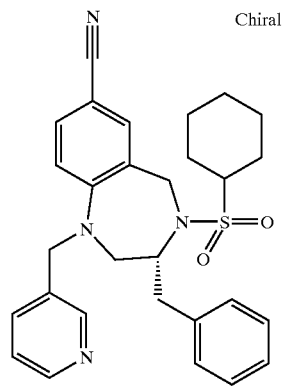

(3R)-2,3,4,5-Tetrahydro-3-(phenylmethyl)-4-(1-piperidinylsulfonyl)-1-(3-pyridinylmethyl)-1H-1,4-benzodiazepine-7-carbonitrile A. Piperidinesulfamyl Chloride The title compound was prepared from piperidine following the procedure of Compound A of Example 37.

$^1$HNMR ($CDCl_3$): 1.54–1.76 (m, 2H), 2.10 (m, 4H), 3.62 (m, 4H).

B. (3R)-2,3,4,5-Tetrahydro-3-(phenylmethyl)-4-(1-piperidinylsulfonyl)-1H-1,4-benzodiazepine-7-carbonitrile The title compound was prepared from Compound A and Compound A of Example 23 following the procedure of Compound B of Example 37.

MS: (M+H)$^+$411.

C. (3R)-2,3,4,5-Tetrahydro-3-(phenylmethyl)-4-(1-piperidinylsulfonyl)-1-(3-pyridinylmethyl)-1H-1,4-benzodiazepine-7-carbonitrile The title compound was prepared from Compound B following the procedure of Compound C of Example 23.

MS: (M+H)$^+$502; Elemental analysis for $C_{28}H_{31}N_5O_2S.0.93HCl.0.92H_2O$; Calc: C, 60.91; H, 6.17;

N, 12.68; S, 5.81; Cl, 5.97; Found: C, 60.91; H, 6.15; N, 12.66; S, 5.77; Cl, 5.97.

EXAMPLE 39

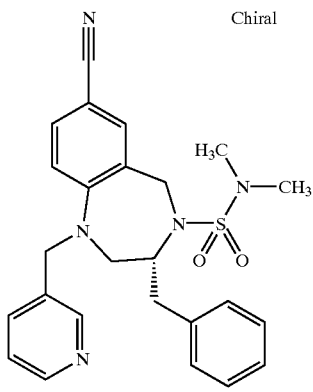

(3R)-7-Cyano-1,2,3,5-tetrahydro-N,N-dimethyl-3-(phenylmethyl)-1-(3-pyridinylmethyl)-4H-1,4-benzodiazepine-4-sulfonamide A. (3R)-7-Cyano-1,2,3,5-tetrahydro-N,N-dimethyl-3-(phenylmethyl)-4H-1,4-benzodiazepine-4-sulfonamide The title compound was prepared from Compound A of Example 23 and dimethylsulfamyl chloride following the procedure of Compound B of Example 37.

HRMS (M+H)+; Calc: 371.1541; Found: 371.1523 (−5.0/−1.9) ppm/mmu.

B. (3R)-7-Cyano-1,2,3,5-tetrahydro-N,N-dimethyl-3-(phenylmethyl)-1-(3-pyridinylmethyl)-4H-1,4-benzodiazepine-4-sulfonamide The title compound was prepared from Compound A following the procedure of Compound C of Example 23.

MS: (M+H)$^+$462; Elemental analysis for $C_{25}H_{27}N_5O_2S.1.4HCl.0.44H_2O$; Calc: C, 57.68; H, 5.67; N, 13.45; Found: C, 57.68; H, 5.67; N, 13.24.

EXAMPLE 40

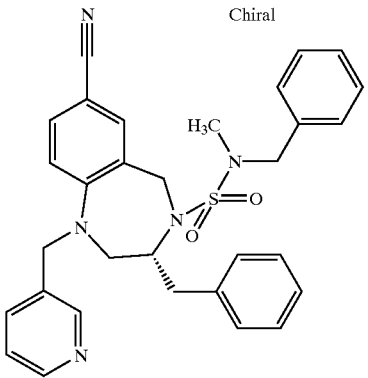

(3R)-7-Cyano-1,2,3,5-tetrahydro-N-methyl-N,3-bis(phenylmethyl)-1-(3-pyridinylmethyl)-4H-1,4-benzodiazepine-4-sulfonamide A. N-Benzylmethylsulfamyl Chloride The title compound was prepared with N-benzylmethylamine following the procedure of Compound A of Example 37.

$^1$HNMR (CDCl$_3$): 2.84 (s, 3H), 4.25–4.45 (br m, 2H), 7.34–7.38 (m, 5H).

B. (3R)-7-Cyano-1,2,3,5-tetrahydro-N-methyl-N,3-bis(phenylmethyl)-4H-1,4-benzodiazepine-4-sulfonamide The title compound was prepared from Compound A and Compound A of Example 23 following the procedure of Compound B of Example 37.

C. (3R)-7-Cyano-1,2,3,5-tetrahydro-N-methyl-N,3-bis(phenylmethyl)-1-(3-pyridinylmethyl)-4H-1,4-benzodiazepine-4-sulfonamide The title compound was prepared from Compound B following the procedure of Compound C of Example 23.

MS: (M+H)$^+$538; Elemental analysis for $C_{31}H_{31}N_5O_2S.1.0HCl$; HRMS: (M+H)$^+$; Calc: 538.22767; Found: 538.2258.

EXAMPLE 41

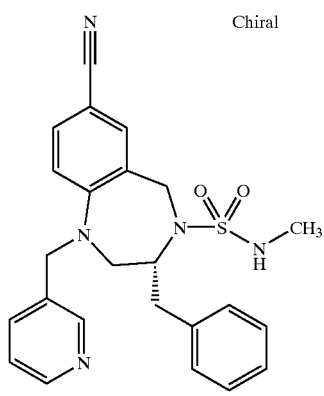

(3R)-7-Cyano-1,2,3,5-tetrahydro-N-methyl-3-(phenylmethyl)-1-(3-pyridinylmethyl)-4H-1,4-benzodiazepine-4-sulfonamide A. Methylsulfamyl Chloride The title compound was prepared from methylamine following the procedure of Compound A of Example 37.

$^1$NMR (CDCl$_3$): 3.04–3.05 (d, 3H, J=5.41), 5.46 (br m, 1H).

B. (3R)-7-Cyano-1,2,3,5-tetrahydro-N-methyl-3-(phenylmethyl)-4H-1,4-benzodiazepine-4-sulfonamide The title compound was prepared from Compound A and Compound A of Example 23 following the procedure of Compound B of Example 37.

MS: (M−H)$^-$355; Elemental analysis for $C_{18}H_{20}N_4O_2S.0.29H_2O$; Calc: C, 59.78; H, 5.74; N, 15.49; S, 8.86; Found: C, 59.77; H, 5.58; N, 15.46; S, 8.82.

C. (3R)-7-Cyano-1,2,3,5-tetrahydro-N-methyl-3-(phenylmethyl)-1-(3-pyridinylmethyl)-4H-1,4-benzodiazepine-4-sulfonamide The title compound was prepared from Compound B following the procedure of Compound C of Example 23.

MS: (M+H)$^+$448; Elemental analysis for $C_{24}H_{25}N_5O_2S.1.13HCl.0.78H_2O$; Calc: C, 57.33; H, 5.55; N, 13.93; S, 6.38; Cl, 7.97; Found: C, 57.33; H, 5.44; N, 13.93; S, 6.26; Cl, 7.98.

EXAMPLE 42

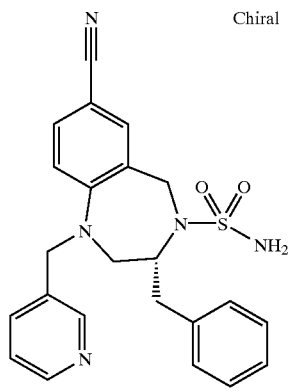

(3R)-7-Cyano-1,2,3,5-tetrahydro-3-(phenylmethyl)-1-(3-pyridinylmethyl)-4H-1,4-benzodiazepine-4-sulfonamide A. (3R)-7-Cyano-1,2,3,5-tetrahydro-3-(phenylmethyl)-4H-1,4-benzodiazepine-4-sulfonamide The title compound was prepared from Compound A of Example 23 and sulfamyl chloride following the procedure of Compound B of Example 37.

MS: $(M-H)^- 341$; Elemental analysis for $C_{17}H_{18}N_4O_2S \cdot 0.50H_2O$; Calc: C, 58.10; H, 5.45; N, 15.94; Found: C, 58.11; H, 5.33; N, 15.67.

B. (3R)-7-Cyano-1,2,3,5-tetrahydro-3-(phenylmethyl)-1-(3-pyridinylmethyl)-4H-1,4-benzodiazepine-4-sulfonamide The title compound was prepared from Compound A following the procedure of Compound C of Example 23.

MS: $(M+H)^+ 434$; Elemental analysis for $C_{23}H_{23}N_5O_2S \cdot 1.05HCl \cdot 0.65H_2O$; Calc: C, 57.13; H, 5.28; N, 14.48; S, 6.63; Cl, 7.70; Found: C, 57.14; H, 5.24; N, 14.51; S, 6.58; Cl, 7.63.

EXAMPLE 43

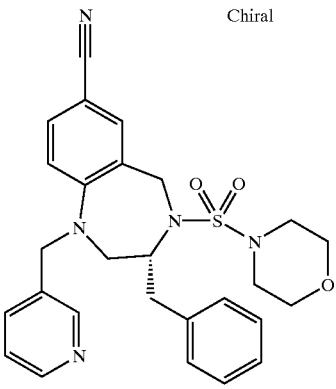

(3R)-2,3,4,5-Tetrahydro-4-(4-morpholinylsulfonyl)-3-(phenylmethyl)-1-(3-pyridinylmethyl)-1H-1,4-benzodiazepine-7-carbonitrile A. Morpholinesulfamyl Chloride The title compound was prepared from morpholine following the procedure of compound A of Example 37.

$^1$HNMR (CDCl$_3$): 3.27–3.37 (m, 4H), 3.85–3.88 (m, 4H).

B. (3R)-2,3,4,5-Tetrahydro-4-(4-morpholinylsulfonyl)-3-(phenylmethyl)-1H-1,4-benzodiazepine-7-carbonitrile The title compound was prepared from Compound A and Compound A of Example 23 following the procedure of Compound B of Example 37.

HRMS (M+H)+; Calc: 413.1647; Found: 413.1614 (−8.1/−3.3) ppm/mmu.

C. (3R)-2,3,4,5-Tetrahydro-4-(4-morpholinylsulfonyl)-3-(phenylmethyl)-1-(3-pyridinylmethyl)-1H-1,4-benzodiazepine-7-carbonitrile The title compound was prepared from Compound B following the procedure of Compound C of Example 23.

MS: $(M+H)^+ 504$; Elemental analysis for $C_{27}H_{29}N_5O_3S \cdot 1.15HCl \cdot 1.14H_2O$; Calc: C, 57.29; H, 5.77; N, 12.37; S, 5.66; Cl, 7.20. Found: C, 57.28; H, 5.67; N, 12.09; S, 5.71; Cl, 7.06.

EXAMPLE 44

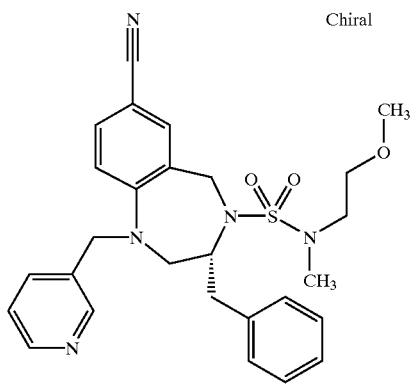

(3R)-7-Cyano-1,2,3,5-tetrahydro-N-(2-methoxyethyl)-N-methyl-3-(phenylmethyl)-1-(3-pyridinylmethyl)-4H-1,4-benzodiazepine-4-sulfonamide A. N-(2-Methoxyethyl)methylsulfamyl Chloride The title compound was prepared from N-(2-methoxyethyl)methylamine following the procedure of Compound A of Example 37.

$^1$HNMR (CDCl$_3$): 3.15–3.30 (m, 1), 3.30–3.50 (m, 4H), 3.50–3.70 (m, 2H).

B. (3R)-7-Cyano-1,2,3,5-tetrahydro-N-(2-methoxyethyl)-N-methyl-3-(phenylmethyl)-4H-1,4-benzodiazepine-4-sulfonamide The title compound was prepared from Compound A and Compound A of Example 23 following the procedure of Compound B of Example 37.

C. (3R)-7-Cyano-1,2,3,5-tetrahydro-N-(2-methoxyethyl)-N-methyl-3-(phenylmethyl)-1-(3-pyridinylmethyl)-4H-1,4-benzodiazepine-4-sulfonamide The title compound was prepared from Compound B following the procedure of Compound C of Example 23.

MS: $(M+H)^+ 506$; HRMS:$(M+H)^+$; Calc: 506.2226; Found: 506.2232 (+1.3 /+0.6) ppm/mmu.

EXAMPLE 45

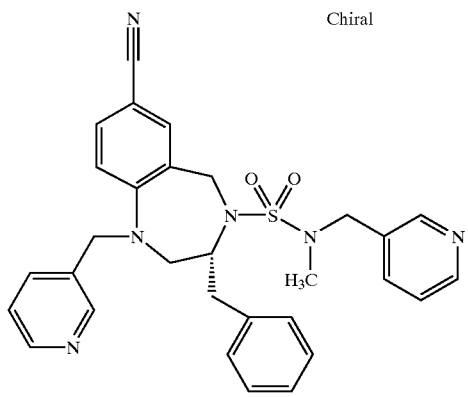

(3R)-7-Cyano-1,2,3,5-tetrahydro-N-methyl-3-(phenylmethyl)-N,1-bis(3-pyridinylmethyl)-4H-1,4-benzodiazepine-4-sulfonamide A. N-(3-Pyridylmethyl)methylsulfamyl Chloride The title compound was prepared from 3-picolylmethylamine following the procedure of Compound A of Example 37.

(M+H)$^+$221.

B. (3R)-7-Cyano-1,2,3,5-tetrahydro-N-methyl-3-(phenylmethyl)-N-(3-pyridinylmethyl)-4H-1,4-benzodiazepine-4-sulfonamide The title compound was prepared from Compound A and Compound A of Example 23 following the procedure of Compound B of Example 37.

MS(M+H)$^+$448.

C. (3R)-7-Cyano-1,2,3,5-tetrahydro-N-methyl-3-(phenylmethyl)-N,1-bis(3-pyridinylmethyl)-4H-1,4-benzodiazepine-4-sulfonamide The title compound was prepared from Compound B following the procedure of Compound C of Example 23.

MS: (M+H)$^+$539; Elemental analysis for $C_{30}H_{30}N_6O_2S \cdot 3.0HCl \cdot 2.69H_2O$; Calc: C, 51.73 H, 5.55; N, 12.07; Found: C, 51.74; H, 5.44; N, 11.80.

EXAMPLE 46

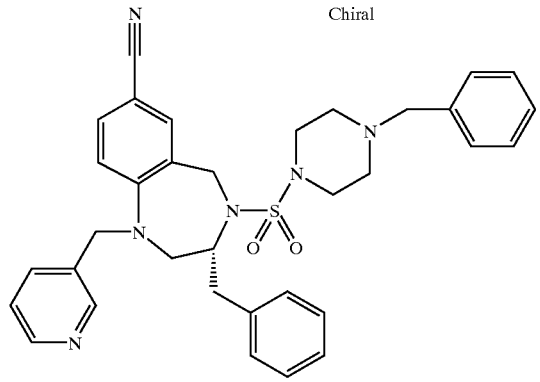

(3R)-2,3,4,5-Tetrahydro-3-(phenylmethyl)-4-[[4-(phenylmethyl)-1-piperazinyl]sulfonyl]-1-(3-pyridinylmethyl)-1H-1,4-benzodiazepine-7-carbonitrile A. 1-Benzylpiperazinesulfamyl Chloride The title compound was prepared from 1-benzylpiperazine following the procedure of Compound A of Example 37.

$^1$HNMR (CDCl$_3$): 2.90–3.10 (m, 2H), 3.50–3.65 (m, 2H), 3.90–4.00 (m, 4H), 4.25 (s, 2H), 7.50–7.55 (m, 3H), 7.60–7.80 (m, 2H).

B. (3R)-2,3,4,5-Tetrahydro-3-(phenylmethyl)-4-[[4-(phenylmethyl)-1-piperazinyl]sulfonyl]-1H-1,4-benzodiazepine-7-carbonitrile The title compound was prepared from Compound A and Compound A of Example 23 following the procedure of Compound B of Example 37.

C. (3R)-2,3,4,5-Tetrahydro-3-(phenylmethyl)-4-[[4-(phenylmethyl)-1-piperazinyl]sulfonyl]-1-(3-pyridinylmethyl)-1H-1,4-benzodiazepine-7-carbonitrile The title compound was prepared from Compound B following the procedure of Compound C of Example 23.

MS: (M+H)$^+$593; Elemental analysis for $C_{34}H_{36}N_6O_2S \cdot 2.12HCl \cdot 2.07H_2O$; Calc: C, 57.50 H, 6.01; N, 11.83; S, 4.51; Cl, 10.98; Found: C, 57.49; H, 5.73; N, 11.71; S, 4.48; Cl, 10.81.

EXAMPLE 47

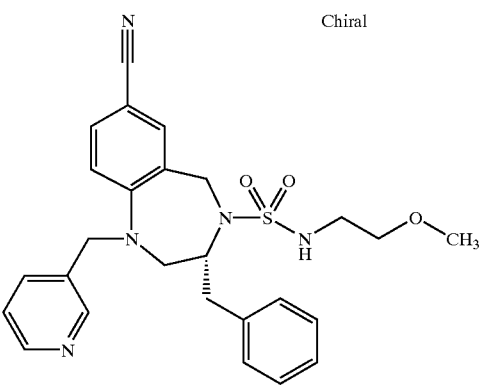

(3R)-7-Cyano-1,2,3,5-tetrahydro-N-(2-methoxyethyl)-3-(phenylmethyl)-1-(3-pyridinylmethyl)-4H-1,4-benzodiazepine-4-sulfonamide A. 2-Methoxyethylsulfamyl Chloride The title compound was prepared from 2-methoxyethylamine following the procedure of Compound A of Example 37.

$^1$HNMR (CDCl$_3$): 3.15–3.30 (m, 1H), 3.30–3.50 (m, 4H), 3.50–3.70 (m, 2H).

B. (3R)-7-Cyano-1,2,3,5-tetrahydro-N-(2-methoxyethyl)-3-(phenylmethyl)-4H-1,4-benzodiazepine-4-sulfonamide The title compound was prepared from Compound A and Compound A of Example 23 following the procedure of Compound B of Example 37.

C. (3R)-7-Cyano-1,2,3,5-tetrahydro-N-(2-methoxyethyl)-3-(phenylmethyl)-1-(3-pyridinylmethyl)-4H-1,4-benzodiazepine-4-sulfonamide The title compound was prepared from Compound B following the procedure of Compound C of Example 23.

MS: (M+H)$^+$492; Elemental analysis for $C_{26}H_{29}N_5O_3S \cdot 1.3HCl \cdot 1.16H_2O$; Calc: C, 55.77 H, 5.87; N, 12.51; S, 5.73; Cl, 8.23; Found: C, 55.78; H, 5.76; N, 12.36; S, 5.69; Cl, 8.10.

EXAMPLE 48

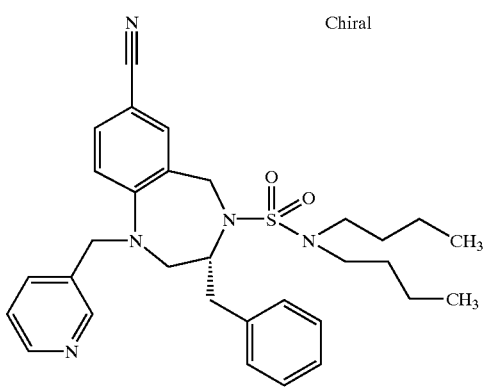

(3R)-N,N-Dibutyl-7-cyano-1,2,3,5-tetrahydro-3-(phenylmethyl)-1-(3-pyridinylmethyl)4H-1,4-benzodiazepine-4-sulfonamide A. Dibutylsulfamyl Chloride The title compound was prepared from dibutylamine following the procedure of Compound A of Example 37.

$^1$HNMR (CDCl$_3$): 0.94–0.98 (m, 6H), 1.33–1.42 (m, 4H), 1.64–1.71 (m, 4H), 3.28–3.32 (m, 4H).

B. (3R)-N,N-Dibutyl-7-cyano-1,2,3,5-tetrahydro-3-(phenylmethyl)-4H-1,4-benzodiazepine4-sulfonamide The title compound was prepared from Compound A and Compound A of Example 23 following the procedure of Compound B of Example 37.

C. (3R)-N,N-Dibutyl-7-cyano-1,2,3,5-tetrahydro-3-(phenylmethyl)-1-(3-pyridinylmethyl)-4H-1,4-benzodiazepine-4-sulfonamide The title compound was prepared from Compound B following the procedure of Compound C of Example 23.

MS: (M+H)$^+$546; Elemental analysis for C$_{31}$H$_{39}$N$_5$O$_2$S.1.0HCl0.57H$_2$O Calc: C, 62.85 H, 7.00; N, 11.82; Cl, 5.98; Found: C, 62.85; H, 7.00; N, 11.77; Cl, 5.72.

What is claimed is:

1. A compound of the formula:

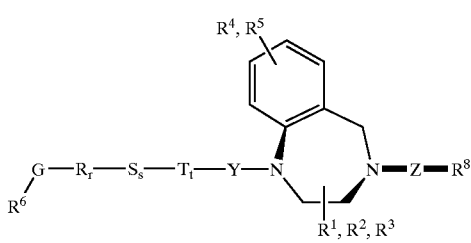

I or its enantiomer, diastereomer, pharmaceutically acceptable salt or solvate thereof, wherein:

r, s and t are each independently 0 or 1;

Z is CHR$^9$, SO$_2$, CO, CO$_2$, O, NR$^{10}$, —SO$_2$NR$^{11}$, —CONR$^{12}$,

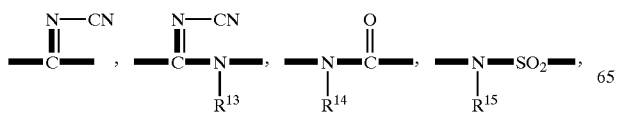

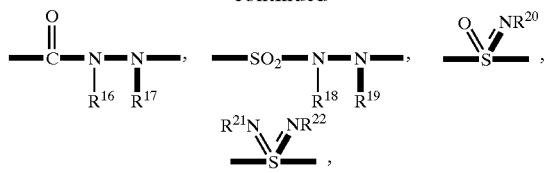

or Z may be absent;

Y is CHR$^{23}$, SO$_2$, CO, NR$^{24}$,

—SO$_2$NR$^{25}$ or —CONR$^{26}$ or Y may be absent;

R$^6$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$, R$^{23}$, R$^{24}$, R$^{25}$, R$^{26}$, R$^{28}$, R$^{29}$, R$^{30}$, R$^{31}$, R$^{32}$, R$^{33}$, R$^{34}$, R$^{35}$, R$^{36}$, R$^{37}$, R$^{38}$, R$^{39}$, R$^{41}$, R$^{42}$, R$^{42}$, R$^{43}$, R$^{44}$, R$^{45}$ and R$^{46}$ are each independently hydrogen, lower alkyl, substituted alkyl, aryl, or substituted aryl;

R$^4$, R$^5$, R$^{47}$, R$^{48}$, R$^{49}$, R$^{50}$ and R$^{51}$ are each independently hydrogen, halo, nitro, cyano or U-R$^{27}$;

U is sulfur, oxygen, NR$^{28}$, CO, SO, SO$_2$, CO$_2$, NR$^{29}$CO$_2$, NR$^{30}$CONR$^{31}$, NR$^{32}$SO$_2$, NR$^{33}$SO$_2$NR$^{34}$, SO$_2$NR$^{35}$, NR$^{36}$CO, CONR$^{37}$, PO$_2$R$^{38}$ or PO$_3$R$^{39}$ or U is absent;

R$^4$ and R$^5$ may join together to form a ring;

R$^1$, R$^2$ and R$^3$ are each independently hydrogen, alkyl, alkoxycarbonyl, substituted alkyl, alkenyl, substituted alkenyl, alkynyl, substituted alkynyl, aralkyl, cycloalkyl, aryl, substituted aryl, heterocyclo, substituted heterocyclo, cyano, carboxy, carbamyl or substituted carbamyl; R$^8$ and R$^{27}$ are each independently hydrogen, alkyl, substituted alkyl, alkenyl, substituted alkenyl, alkynyl, substituted alkynyl, aralkyl, cycloalkyl, aryl, substituted aryl, heterocyclo or substituted heterocyclo;

any two of R$^1$, R$^2$ and R$^3$ may join to form a cycloalkyl group;

R, S and T are each independently CR$^{40}$R$^{41}$ or NR$_{42}$;

R$^{40}$ is H, NR$_{44}$R$^{45}$, OR$^{46}$ or CN;

G is —S—, —SO$_2$NH—, —NHSO$_2$—, —N(OR$^{46}$)SO$_2$—,

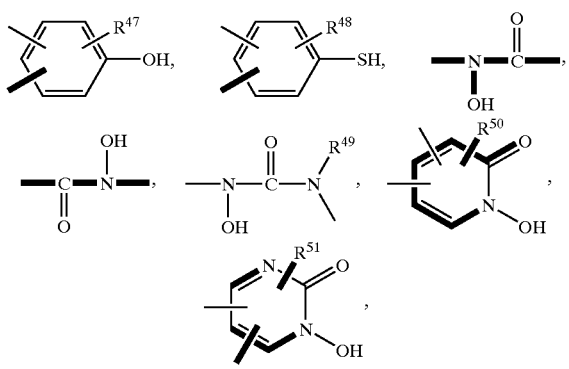

or heterocycles other than imidazole;

with the provisos that:

1) R$^{27}$ may be hydrogen except when U is SO, SO$_2$, CO$_2$, NR$^{29}$CO$_2$ or NR$^{32}$SO$_2$;

2) $R^8$ may be hydrogen except when Z is $SO_2$, $CO_2$,

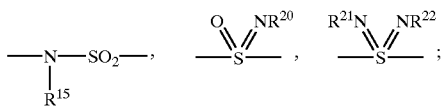

3) only one of Y, R, S and T may be nitrogen;
4) any of Y, R, S and T may be nitrogen except when G is —S—, —NHSO$_2$—, —N(OR$^{46}$)SO$_2$—,

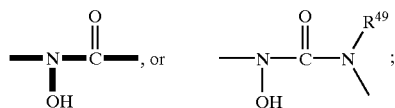

5) $R^6$ may be hydrogen except when G is —NHSO$_2$— or —N(OR$_{46}$)SO$_2$—; or
6) the sum of r, s and t together may not be zero.

2. A compound selected from the group consisting of (+, −)-1-(2-Amino-3-mercaptopropyl)-2,3,4,5-tetrahydro-4-(naphthalenylcarbonyl)-1H-1,4-benzodiazepine, monohydrochloride;

(+,−)-1-(2-Amino-3-mercaptopropyl)-2,3,4,5-tetrahydro-4-(naphthalenylcarbonyl)-7-phenyl-1H-1,4-benzodiazepine, monohydrochloride;

2,3,4,5-Tetrahydro-4-(1-naphthalenylsulfonyl)-N-(3-pyridinyl)-1H-1,4-benzodiazepine-1-carboxamide;

(R)-7-Bromo-2,3,4,5-tetrahydro-4-(methylsulfonyl)-1-[(2-oxo-1-pyrrolidinyl)acetyl]-3-(phenylmethyl)-1H-1,4-benzodiazepine, trifluoroacetate;

(R)-7-Bromo-4-[[2-(dimethylamino)ethyl]sulfonyl]-2,3,4,5-tetrahydro-β-oxo-3-(phenylmethyl)-1H-1,4-benzodiazepine-1-ethanesulfonamide;

2,3,4,5-Tetrahydro-4-(1-naphthalenylcarbonyl)-1-(2-thienylmethyl)-1H-1,4-benzodiazepine;

2,3,4,5-Tetrahydro-4-(1-naphthalenylcarbonyl)-1-(3-pyridinylmethyl)-7-phenyl-1H-1,4-benzodiazepine, hydrochloride;

2,3,4,5-Tetrahydro-4-(1-naphthalenylcarbonyl)-1-(3-thienylmethyl)-1H-1,4-benzodiazepine;

2,3,4,5-Tetrahydro-1-[2-(3-hydroxy-2-oxo-1(2H)-pyridinyl)ethyl]-4-(1-naphthalenylcarbonyl)-7-1,4-benzodiazepine, dihydrochloride;

2,3,4,5-Tetrahydro-1-[2-(3-hydroxy-2-oxo-1(2H)-pyridinyl)ethyl]-4-(1-naphthalenylcarbonyl)-7-phenyl-1H-1,4-benzodiazepine, dihydrochloride;

2,3,4,5-Tetrahydro-4-(1-naphthalenylcarbonyl)-1-[(5-oxo-2-pyrrolidinyl)carbonyl]-7-phenyl-1H-1,4-benzodiazepine;

2,3,4,5-Tetrahydro-4-(1-naphthalenylcarbonyl)-7-phenyl-1-[3-(2-pyridinylamino)propyl]-1H-1,4-benzodiazepine, dihydrochloride;

2,3,4,5-Tetrahydro-4-(1-naphthalenylcarbonyl)-7-phenyl-1-[3-(3-pyridinylamino)propyl]-1H-1,4-benzodiazepine, dihydrochloride;

2,3,4,5-Tetrahydro-4-(1-naphthalenylcarbonyl)-7-phenyl-1-[3-(1H-pyrazol-3-ylamino)propyl]-1H-1,4-benzodiazepine, dihydrochloride;

2,3,4,5-Tetrahydro-4-(1-naphthalenylcarbonyl)-7-phenyl-1-[3-(2-pyrimidinylamino)propyl]-1H-1,4-benzodiazepine, dihydrochloride;

(R)-7-Bromo-2,3,4,5-tetrahydro-4-(methylsulfonyl)-1-(3-pyridinylmethyl)-3-(phenylmethyl)-1H-1,4-benzodiazepine, hydrochloride;

(R)-7-Bromo-2,3,4,5-tetrahydro-4-(methylsulfonyl)-1-(1-oxo-3-pyridinylmethyl)-3-(phenylmethyl)-1H-1,4-benzodiazepine, hydrochloride;

(R)-7-Bromo-2,3,4,5-tetrahydro-4-(methylsulfonyl)-1-(2-pyridinylmethyl)-3-(phenylmethyl)-1H-1,4-benzodiazepine, hydrochloride;

(R)-7-Bromo-2,3,4,5-tetrahydro-4-(methylsulfonyl)-1-(4-pyridinylmethyl)-3-(phenylmethyl)-1H-1,4-benzodiazepine, hydrochloride;

(R)-7-Bromo-2,3,4,5-tetrahydro-N-hydroxy-4-(methylsulfonyl)-1H-1,4-benzodiazepine-1-acetamide, hydrochloride;

(R)-7,9-Dibromo-2,3,4,5-tetrahydro-4-(methylsulfonyl)-1-(3-pyridinylmethyl)-3-(phenylmethyl)-1H-1,4-benzodiazepine, hydrochloride;

(R)-7-Bromo-9-chloro-2,3,4,5-tetrahydro-4-(methylsulfonyl)-1-(3-pyridinylmethyl)-3-(phenylmethyl)-1H-1,4-benzodiazepine, hydrochloride;

(R)-7-Cyano-2,3,4,5-tetrahydro-3-(phenylmethyl)-1-(3-pyridinylmethyl)-4-(2-thienesulfonyl)-1H-1,4-benzodiazepine, hydrochloride;

(R)-7-Cyano-2,3,4,5-tetrahydro-1-(4-butylthio)-3-(phenylmethyl)-4-(2-thienylsulfonyl)-1H-1,4-benzodiazepine;

(R)-7-Cyano-4-[[2-(dimethylamino)ethyl]sulfonyl]-2,3,4,5-tetrahydro-1-(5-oxazolylmethyl)-3-(phenylmethyl)-1H-1,4-benzodiazepine;

(R)-7-Cyano-4-[[2-(dimethylamino)ethyl]sulfonyl]-2,3,4,5-tetrahydro-1-(5-isoxazolylmethy)-3-(phenylmethyl)-1H-1,4-benzodiazepine;

(R)-7-Cyano-2,3,4,5-tetrahydro-1-(2-mercaptoethyl)-3-(phenylmethyl)-4-(propylsulfonyl)-1H-1,4-benzodiazepine;

(R)-N-[2-[7-Cyano-2,3,4,5-tetrahydro-3-(phenylmethyl)-4-(propylsulfonyl)-1H-1,4-benzodiazepin-1-yl]ethyl]trifluoromethanesulfonamide;

(R)-N-[2-[7-Cyano-2,3,4,5-tetrahydro-3-(phenylmethyl)-4-(propylsulfonyl)-1H-1,4-benzodiazepin-1-yl]ethyl]methanesulfonamide;

(3R)-2,3,4,5-Tetrahydro-4-[(1-methyl-1H-pyrazol-4-yl)sulfonyl]-3-(phenylmethyl)-1-(3-pyridinylmethyl)-1H-1,4-benzodiazepine-7-carbonitrile;

(3R)-2,3,4,5-Tetrahydro-4-[(4-methoxyphenyl)sulfonyl]-3-(phenylmethyl)-1-(3-pyridinylmethyl)-1H-1,4-benzodiazepine-7-carbonitrile;

(3R)-2,3,4,5-Tetrahydro-3-(phenylmethyl)-4-(propylsulfonyl)-1-(3-pyridinylmethyl)-1H-1,4-benzodiazepine-7-carbonitrile;

(3R)-2,3,4,5-Tetrahydro-4-[(4-methylphenyl)sulfonyl]-3-(phenylmethyl)-1-(3-pyridinylmethyl)-1H-1,4-benzodiazepine-7-carbonitrile;

(3R)-4-[(4-Fluorophenyl)sulfonyl]-2,3,4,5-tetrahydro-3-(phenylmethyl)-1-(3-pyridinylmethyl)-1H-1,4-benzodiazepine-7-carbonitrile;

(3R)-7-Cyano-1,2,3,5-tetrahydro-N,N-bis(2-methoxyethyl)-3-(phenylmethyl)-1-(3-pyridinylmethyl)-4H-1,4-benzodiazepine-4-sulfonamide;

(3R)-2,3,4,5-Tetrahydro-3-(phenylmethyl)-4-(1-piperidinylsulfonyl)-1-(3-pyridinylmethyl)-1H-1,4-benzodiazepine-7-carbonitrile;

(3R)-7-Cyano-1,2,3,5-tetrahydro-N,N-dimethyl-3-(phenylmethyl)-1-(3-pyridinylmethyl)-4H-1,4-benzodiazepine-4-sulfonamide;

(3R)-7-Cyano-1,2,3,5-tetrahydro-N-methyl-N,3-bis(phenylmethyl)-1-(3-pyridinylmethyl)-4H-1,4-benzodiazepine-4-sulfonamide;

(3R)-7-Cyano-1,2,3,5-tetrahydro-N-methyl-3-(phenylmethyl)-1-(3-pyridinylmethyl)-4H-1,4-benzodiazepine-4-sulfonamide;

(3R)-7-Cyano-1,2,3,5-tetrahydro-3-(phenylmethyl)-1-(3-pyridinylmethyl)-4H-1,4-benzodiazepine-4-sulfonamide;

(3R)-2,3,4,5-Tetrahydro-4-(4-morpholinylsulfonyl)-3-(phenylmethyl)-1-(3-pyridinylmethyl)-1H-1,4-benzodiazepine-7-carbonitrile;

(3R)-7-Cyano-1,2,3,5-tetrahydro-N-(2-methoxyethyl)-N-methyl-3-(phenylmethyl)-1-(3-pyridinylmethyl)-4H-1,4-benzodiazepine-4-sulfonamide;

(3R)-7-Cyano-1,2,3,5-tetrahydro-N-methyl-3-(phenylmethyl)-N,1-bis(3-pyridinylmethyl)-4H-1,4-benzodiazepine-4-sulfonamide;

(3R)-2,3,4,5-Tetrahydro-3-(phenylmethyl)-4-[[4-(phenylmethyl)-1-piperazinyl]sulfonyl]-1-(3-pyridinylmethyl)-1H-1,4-benzodiazepine-7-carbonitrile;

(3R)-7-Cyano-1,2,3,5-tetrahydro-N-(2-methoxyethyl)-3-(phenylmethyl)-1-(3-pyridinylmethyl)-4H-1,4-benzodiazepine-4-sulfonamide; and (3R)-N,N-Dibutyl-7-cyano-1,2,3,5-tetrahydro-3-(phenylmethyl)-1-(3-pyridinylmethyl)4H-1,4-benzodiazepine-4-sulfonamide.

3. A method of inhibiting farnesyl protein transferase which comprises administering to a mammal in need of such treatment an effective farnesyl protein transferase inhibiting amount of a compound of claim 1 or 2.

4. A method of inhibiting prenyl transferase which comprises administering to a mammal in need of such treatment an effective prenyl transferase inhibiting amount of a compound of claim 1 or 2.

\* \* \* \* \*

UNITED STATES PATENT AND TRADEMARK OFFICE
CERTIFICATE OF CORRECTION

PATENT NO.    : 6,458,783 B1
DATED         : October 1, 2002
INVENTOR(S)   : Ding et al.

Page 1 of 1

It is certified that error appears in the above-identified patent and that said Letters Patent is hereby corrected as shown below:

Column 44,
Line 16, "$R^{42}$, $R^{42}$" should be replaced with -- $R^{42}$ --;

Lines 55-63, the chemical structure " 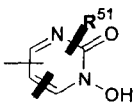 " should be replaced with the chemical structure -- 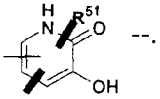 --.

Column 45,
Lines 43-45, "2,3,4,5-Tetrahydro-1-[2-(3-hydroxy-2-oxo-1(2H)-pyridinyl)ethyl]-4-(1-naphthalenylcarbonyl)-7-1,4-benzodiazepine, dihydrochloride" should be replaced with -- 2,3,4,5-Tetrahydro-1-[2-(3-hydroxy-2-oxo-1(2H)-pyridinyl)ethyl]-4-(1-naphthalenylcarbonyl)-1H-1,4-benzodiazepine, dihydrochloride --.

Signed and Sealed this

Twenty-seventh Day of September, 2005

JON W. DUDAS
*Director of the United States Patent and Trademark Office*